United States Patent
Tanaka et al.

(10) Patent No.: US 7,166,839 B2
(45) Date of Patent: Jan. 23, 2007

(54) APPARATUS FOR MEASURING A THREE-DIMENSIONAL SHAPE

(75) Inventors: Maki Tanaka, Yokohama (JP); Chie Shishido, Yokohama (JP); Yuji Takagi, Kamakura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/320,752

(22) Filed: Dec. 30, 2005

(65) Prior Publication Data

US 2006/0108526 A1 May 25, 2006

Related U.S. Application Data

(62) Division of application No. 10/460,217, filed on Jun. 13, 2003, now Pat. No. 6,984,589.

(30) Foreign Application Priority Data

Jun. 13, 2002 (JP) .............................. 2002-172198

(51) Int. Cl.
*G21K 7/00* (2006.01)
(52) U.S. Cl. ............... 250/310; 250/307; 250/252.1 R; 250/306; 250/311; 250/252 R; 250/442.11; 250/397; 438/714; 73/105
(58) Field of Classification Search .................. None
See application file for complete search history.

(56) References Cited

U.S. PATENT DOCUMENTS 6,472,662 B1 10/2002 Archie 7,067,808 B1 * 6/2006 Kochi et al. ................. 250/307

OTHER PUBLICATIONS

Electron Beam Testing Handbook, Electron Beam Research 7th Volume, Committee No. 132, the 98th Research Material, pp. 261, May 1987.

* cited by examiner

*Primary Examiner*—Nikita Wells
*Assistant Examiner*—Zia R. Hashmi
(74) *Attorney, Agent, or Firm*—Antonelli, Terry, Stout and Kraus, LLP.

(57) ABSTRACT

Conventionally, there is no method for quantitatively evaluating the three-dimensional shape of an etched pattern in a non-destructive manner and it takes much time and costs to determine etching conditions. With the conventional length measuring method only, it has been impossible to detect an abnormality in the three-dimensional shape and also difficult to control the etching process. According to the present invention, variations in signal amounts of an SEM image are utilized to compute three-dimensional shape data on the pattern associated with the etching process steps, whereby the three-dimensional shape is quantitatively evaluated. Besides, determination of etching process conditions and process control are performed based on the three-dimensional shape data obtained. The present invention makes it is possible to quantitatively evaluate the three-dimensional shape of the etched pattern in a non-destructive manner. Further, the efficiency of determining the etching process conditions and a stable etching process can be realized.

6 Claims, 25 Drawing Sheets

NORMAL

TAPERED

SIDEWALL ANGLE $\theta$

RETROGRADE

BOTTOM CORNER ROUNDNESS

Poly Si

SiO2 (GATE OXIDE)

Si Substrate

DEVELOPMENT

BARC ETCH

Poly Si ETCH STEP 1

Poly Si ETCH STEP 2

PHOTORESIST ASHING th = min + (max − min) × a
a: PREDETERMINED RATIO (0.0~1.0)

TAPERED

BOTTOM CORNER ROUNDNESS

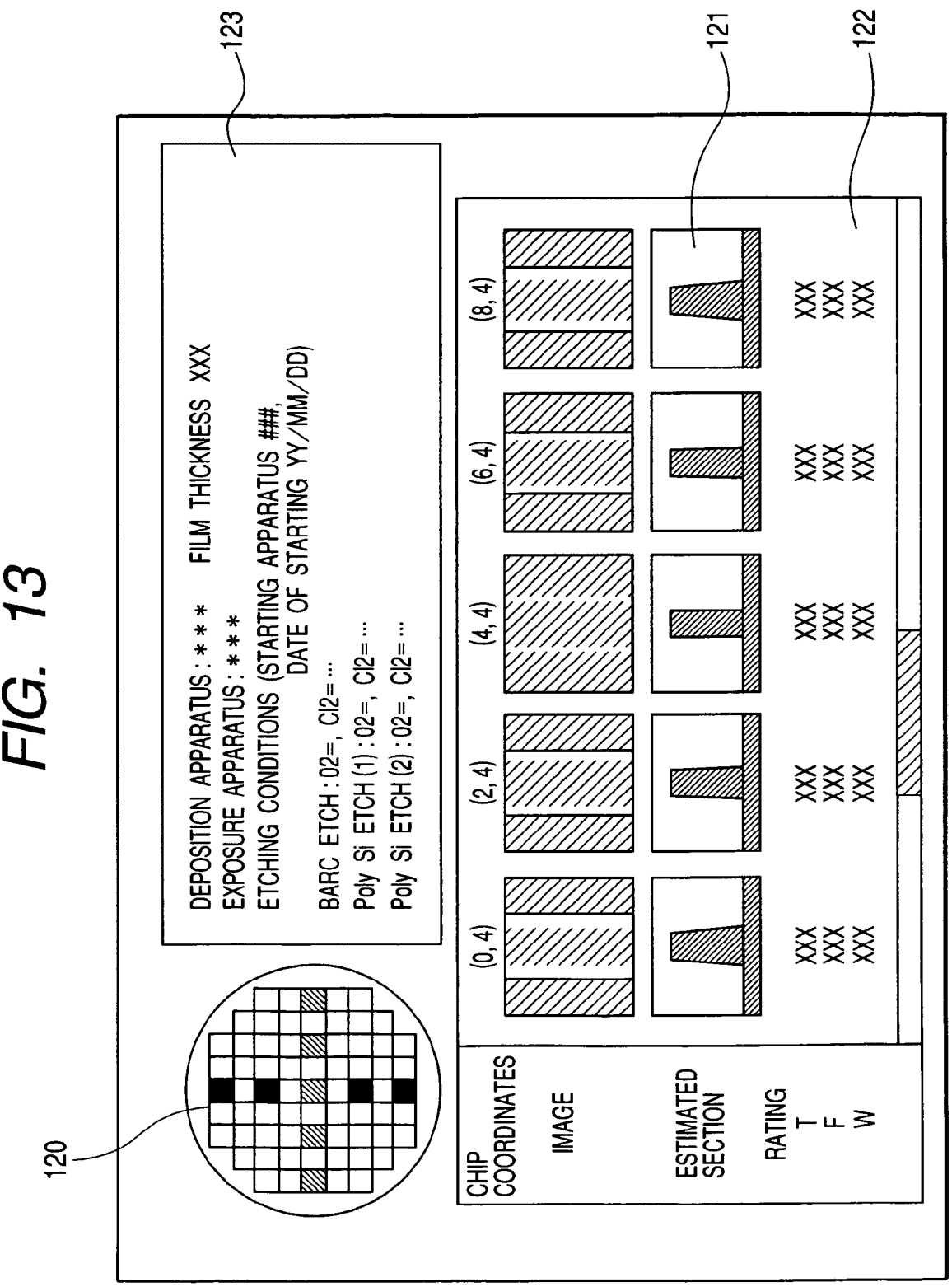

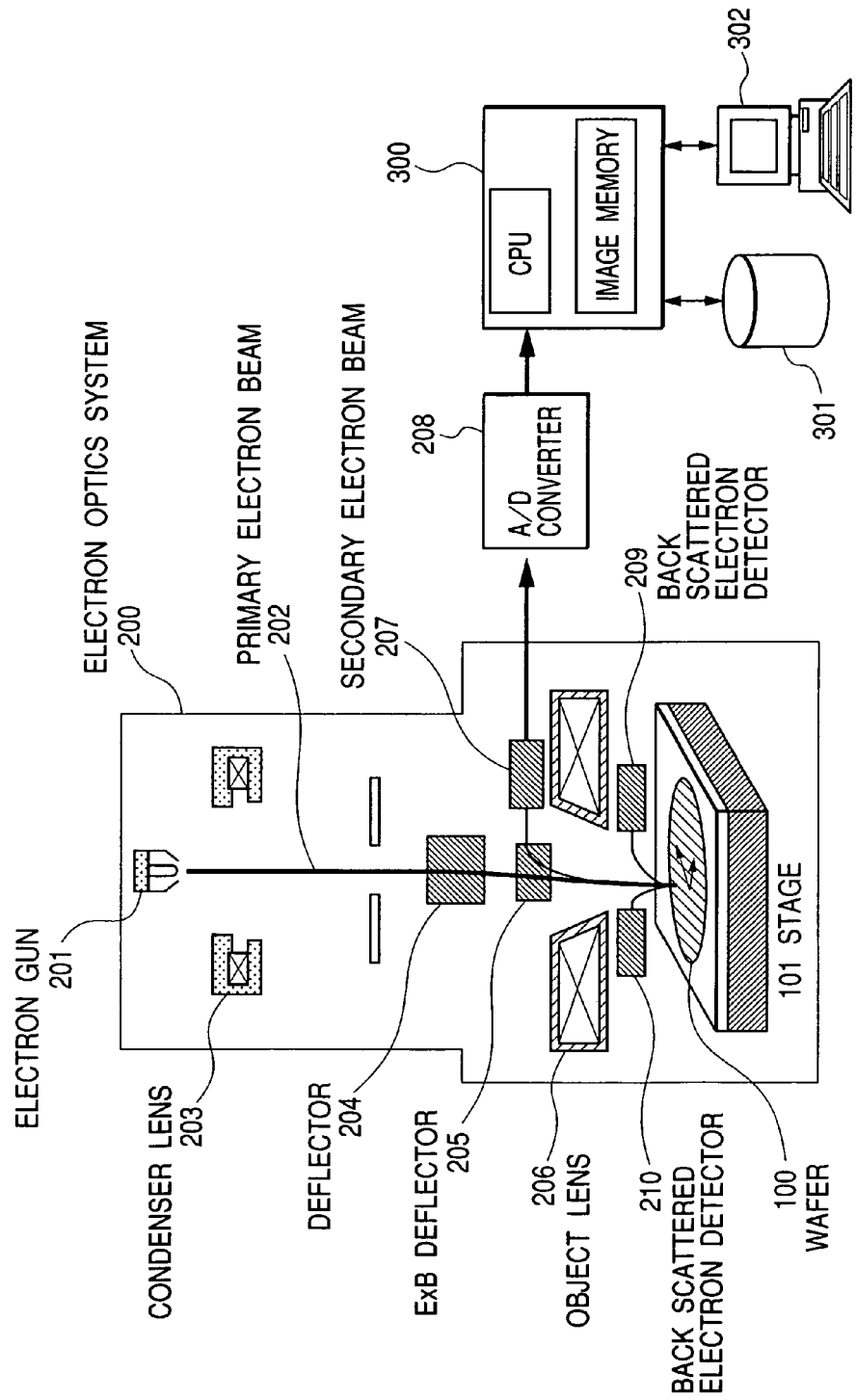

FIG. 24A
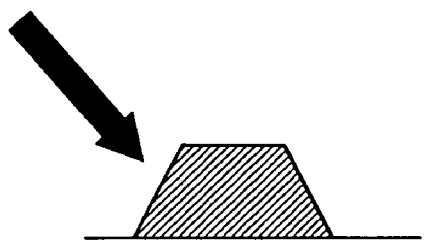
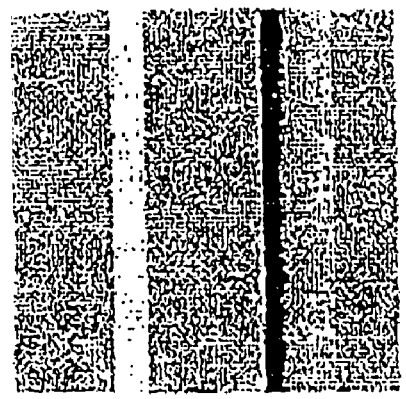
FIG. 24B
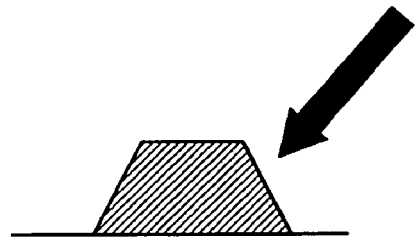
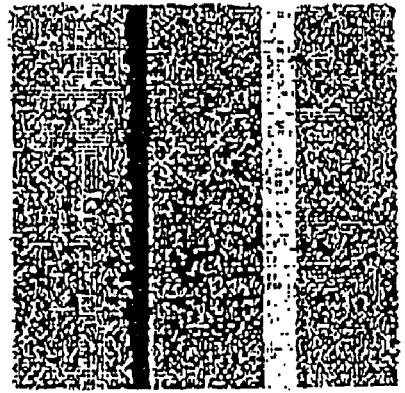

APPARATUS FOR MEASURING A THREE-DIMENSIONAL SHAPE

CROSS REFERENCE TO RELATED APPLICATIONS

This application is a divisional application of U.S. application Ser. No. 10/460,217, filed Jun. 13, 2003 now U.S. Pat. No. 6,984,589, the contents of which are incorporated herein by reference.

BACKGROUND OF THE INVENTION

The present invention relates to a method, and a system therefor, for evaluating the acceptability of the processed shape of a circuit pattern formed on a wafer in a semiconductor manufacturing process, by use of an electron beam image of the circuit pattern.

In order to obtain a desired process performance in an etching step, generally, a confirmation experiment is preliminarily conducted by use of a plurality of process conditions as parameters, then process conditions seeming optimum are determined, and the process conditions are registered as a recipe in an etcher. In the process of determining the process conditions, the acceptability of the etching performance is confirmed principally by observation of a section of the pattern.

FIGS. 2A to 2D show examples of differences in the pattern sectional shape after etching. FIGS. 2A to 2D each show a sectional view of a gate wiring, and the shapes vary depending on the process conditions. In general, in a gate processing step, the shape of the bottom of the pattern affects the results of the subsequent ion implantation step, and the size of the bottom of the pattern itself has a great influence on the device characteristics obtained, so that control of the pattern bottom shape is very important. FIG. 2A shows a shape which is generally considered to be the best, in which the sidewall angle is substantially rectangular, and there is no roundness at the bottom corner. In contrast to this, a tapered shape shown in FIG. 2B, a retrograde shape in FIG. 2C, and a bottom corner roundness in FIG. 2D are shape abnormalities generated due to inappropriate process conditions, and, in these cases, it is necessary to realize the processed condition of FIG. 2A by modifying the process conditions.

Next, referring to FIGS. 3A to 3E, an outline of the gate etching step and the relationship between process conditions and finished shape will be described. Based on a photoresist pattern formed in a photoresist step, etching of the film to be processed is carried out. In a micro-fine process in recent years, generally, a BARC (Bottom Anti-Reflective Coating) layer is provided beneath the photoresist in many cases, and FIGS. 3A to 3E show an example of this case. Here, examples of a BARC etch 1 step and a poly Si etch 2 step are shown; in practice, many other steps may further be used for the gate etching.

After exposure and development, as shown in FIG. 3A, a BARC layer is present on the film to be processed (the poly Si film in FIGS. 3A to 3E), and a photoresist pattern has been formed thereon. In an ordinary production line, the size of the photoresist pattern in this condition is measured, and it is checked whether an abnormal condition is present or absence in the exposure and development step. In the subsequent etching step, etching of the BARC layer is first conducted (FIG. 3B). Next, etching of the poly Si film is conducted by using the photoresist pattern and the BARC film pattern as a mask and changing over the etching conditions. In this instance, the etching of the poly Si film is generally conducted in several divisional steps. First, vertical processing is conducted under a comparatively higher anisotropic condition (Poly Si etch step 1 shown in FIG. 3C), and, near the bottom, processing is conducted by switching to a condition for a higher selectivity ratio between the poly Si film and an oxide film as a substrate (Poly Si etch step 2 shown in FIG. 3D) so that breaking through the oxide film or damaging thereof would not occur, even a little sacrificing the anisotropy. These processings shown in FIGS. 3B to 3D are continuously conducted by changing over the process conditions in a single etcher. After the etching process, the photoresist is removed by photoresist ashing and cleaning, resulting in the formation of a gate pattern as shown in FIG. 3E. Thus, several of the process conditions are changed over during a series of processings, so that in evaluation of the processed results by use of photographs of sections, it is necessary not only to check the presence or absence of abnormalities but also to determine the questionable steps. For example, where an abnormality is present in the sidewall angle, it is judged that the poly Si etch step 1 is the principal cause, and where there is a bottom corner roundness, it is judged that the poly Si etch step 2 is the cause. Based on such judgment, the conditions of each step are optimized.

When the process conditions are determined by the operation for determining the process conditions, the process conditions thus determined are registered in the recipe in the etcher, and the actual etching process in the production line is conducted according to the recipe. It is ideal that the etching performance at this time is quite the same as that in the preliminary determination of the process conditions, but a change in etching rate and the like occur due to time variations in the inside wall condition of an etching chamber, the atmosphere, etc. Attendant on the increase in the degree of integration of LSIs in recent years, there is a demand for a process performance capable of coping with an increase in the fineness of processed sizes and an increase in aspect ratio, and a high-accuracy process control taking shape differences into account in view of such process variations is desired. At present, detection of variations in the pattern shape generated due to the variations in the etching conditions is carried out by measurement of sizes under a length measuring SEM or by picking up SEM images with different inclination angles and measuring the three-dimensional shape based on the principle of stereoscopy.

As has been described above, in the conventional determination of process conditions, the acceptability of the processed shape has been checked by observation of sections of the pattern. However, since the checking of the sectional shape is conducted by cleaving the wafer and using a sectional SEM or the like, the checking requires a very long time and it is difficult to determine the process conditions efficiently. The operations of preparing a specimen for observation of the section and observing the section require a technique different from that for the determination of etching conditions, and are high in cost. In addition, since the conventional method is a destructive evaluation, the wafer having been subjected to the observation must simply be discarded. Not only for the determination of process conditions but also for process control, nondestructive shape evaluation is indispensable. In contrast, the size measurement by use of the length measuring SEM is nondestructive and can be carried out easily. However, there is the problem that only the differences in pattern sizes can simply be found, so that it is impossible to obtain sufficient information for setting the conditions of the etching step.

Now, the problems involved in the conventional shape evaluation (size measurement) by SEM, which are technical problems to be solved by the present invention, will be shown below.

The size measurement on a length measuring SEM is generally conducted by use of a line profile of a secondary electron image. Accordingly, first, the general relationship between a sectional shape and a line profile of secondary electron intensity, as described in Japan Association for the Promotion of Science, Application of Charged Particle Beams to Industry, Committee No. 132, the 98th research material "Electron Beam Testing Handbook", p. 261, will be introduced here.

In FIG. 4,

A) when a substrate portion is irradiated with an electron beam, the intensity of the detected secondary electron signal shows a constant value determined by the discharge efficiency of the secondary electrons from the substrate material;

B) as the point of irradiation with the beam approaches the pattern, the number of those of the secondary electrons generated which collide against the slope portion of the pattern increases, whereby the trap efficiency of the secondary electrons is lowered and, therefore, the signal intensity is somewhat lowered; and C) the intensity of the secondary electron signal shows a minimum value at a position shifted by one half of beam diameter from the bottom edge of the pattern.

D) After passing through point C, the signal intensity abruptly increases substantially linearly due to variations in secondary electron discharge efficiency associated with variations in the slope angle of the specimen; and E) as the point of irradiation with the beam approaches the top edge, the increase of the signal intensity becomes moderate due to the difference in trap coefficient of the secondary electrons discharged from each point of irradiation of the slope portion.

F) The secondary electron signal intensity shows a maximum value at a position shifted by one half of beam diameter to the outer side from the top edge of the pattern; and G) After passing through point F, the signal intensity is gradually lowered, to be settled at a constant value determined by the secondary electron discharge efficiency of the pattern material.

FIG. 4 shows the case of a photoresist, but the same or similar thing can be said in the cases of other materials.

In order to measure the size from such a line profile, it is necessary to detect the edge positions of the pattern from the line profile. As a method for detecting the edge positions mounted on a length measuring SEM, there are known a method of detecting maximum inclination positions as shown in FIG. 5A (maximum inclination method), a threshold method of detecting the edge positions by use of a predetermined threshold as shown in FIG. 5B, and a straight line approximation method of detecting intersections between straight lines fitted to edge portions and substrate portions as shown in FIG. 5C.

However, in the systems of FIGS. 5A and 5B, it is impossible to accurately know what height portion of the actual pattern section is the portion of which the size is being measured. Since the problem in the etching step is the difference in the pattern shape, as shown in FIGS. 2A to 2D, it is necessary to secure a method for making clear what height edge position is being detected. In addition, although the size substantially at the pattern bottom can be measured by the straight line approximation method of FIG. 5C in the case of a sample having a waveform as shown in FIG. 4, it is not necessarily possible, depending on the shape of the waveform, to obtain correct measurements. The secondary electron signal amount obtained with an SEM depends on the slope angle of the pattern surface, and, therefore, in the case where the slope angle at the sidewall of the pattern varies or in other similar cases, the shape of the waveform is not rectilinear, and it is impossible to measure the correct size by the straight line approximation method. Besides, even by measuring the width at either of the top and the bottom of the pattern, it is impossible to correctly evaluate the conditions of the etching step. This is because shape data associated with each of the steps are needed to determine which step is questionable, as shown in FIGS. 3A to 3E. It is difficult to sufficiently obtain data useful for determining the etching conditions, even by use of the three-dimensional shape measuring method utilizing stereoscopy which is effective for obtaining three-dimensional data. For carrying out the stereoscopy, it is necessary to determine points which are associated with each other between two or more images differing in the angle of irradiation with a beam. However, in the case where the pattern shape varies continuously and smoothly, as in the case of a pattern bottom portion shown in FIG. 3E, there is the problem that it is impossible to obtain appropriate corresponding points and, therefore, to achieve satisfactory evaluation.

SUMMARY OF THE INVENTION

According to the present invention, the obtaining of pattern sectional shape data effective for determination of etching process condition, which has not been achieved satisfactorily by the conventional methods, is carried out by use of in-line SEM images which can be observed in a nondestructive manner. Besides, in the present invention, instead of the high-cost section observation, an SEM technique being nondestructive and promising a comparatively easy measurement is used to obtain sectional shape data, thereby realizing efficient process condition determination and process control.

Specifically, according to the present invention, a signal waveform obtained by an electron beam irradiation means for scanningly irradiating a specimen under measurement with a converged electron beam, a signal detecting means for detecting secondary electrons generated from the specimen upon irradiation with the electron beam, and a signal computing means for performing an arithmetic operation on a signal from the signal detecting means is divided into a plurality of regions based on variations in the signal quantity, and the three-dimensional shape of the specimen under measurement is quantitatively evaluated according to the sizes of the divisional regions. In addition, the sectional shape of the pattern is also quantitatively estimated, based on the sizes of the signal waveform thus divided.

In addition, according to the present invention, the three-dimensional shape data on the pattern evaluated and estimated by the above means are made to be associated with etching steps, and the relationships between the etching conditions and the pattern shape are quantitatively evaluated, thereby determining the process conditions and controlling the process.

Furthermore, according to the present invention, also by evaluation of the pattern shape by use of a tilted image and a backscattered electron image, the pattern shape is similarly evaluated and the determination of process conditions and the process control are realized.

These and other objects, features and advantages of the invention will be apparent from the following more particular description of preferred embodiments of the invention, as illustrated in the accompanying drawings.

BRIEF DESCRIPTION OF THE DRAWINGS

FIG. 13 illustrates a method of displaying the results of obtainment of three-dimensional shape data in the first embodiment of the present invention;

FIG. 23 illustrates an SEM having a backscattered electron detecting function in a sixth embodiment of the present invention; and FIGS. 24A and 24B illustrate backscattered electron images (shaded images) according to the sixth embodiment of the present invention.

DETAILED DESCRIPTION OF THE PREFERRED EMBODIMENTS

Figure 1:
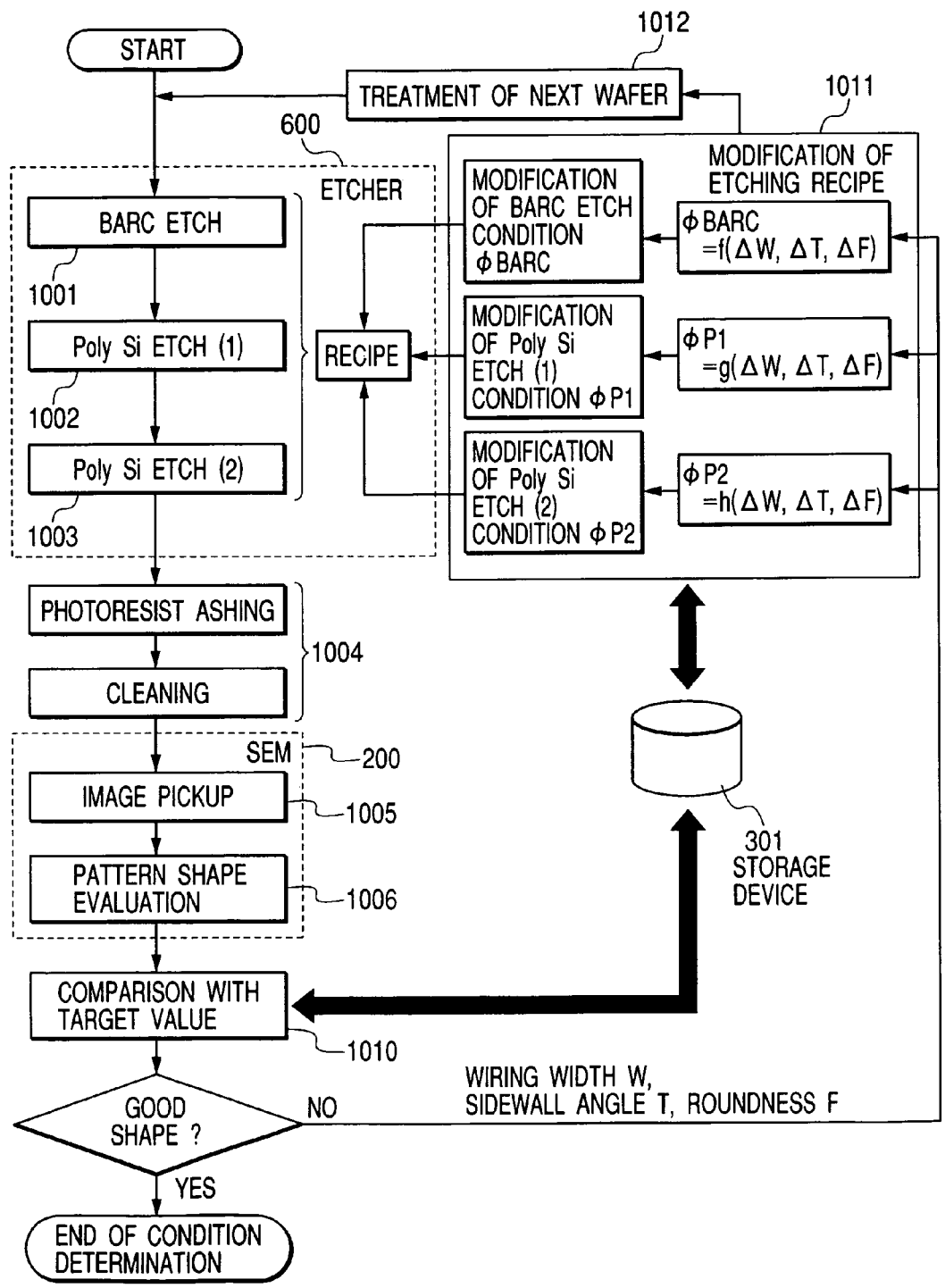
FIG. 1 illustrates the procedure of determining etching conditions in a second embodiment of the present invention.

Now, embodiments of the present invention will be described below referring to the drawings.

Figure 6:
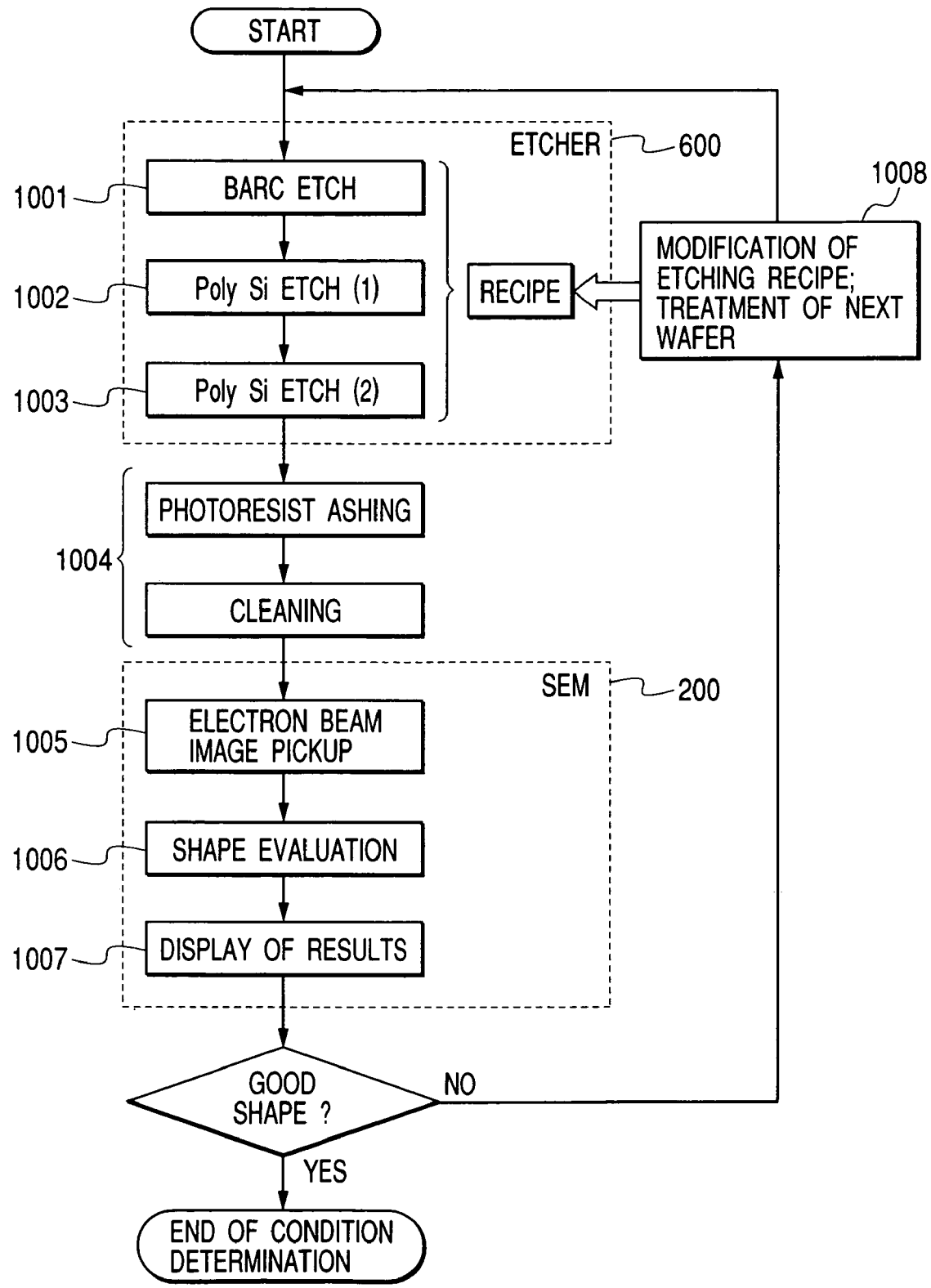
FIG. 6 is a flow sheet of the procedure of determining etching conditions in a first embodiment of the present invention.
Figure 10:
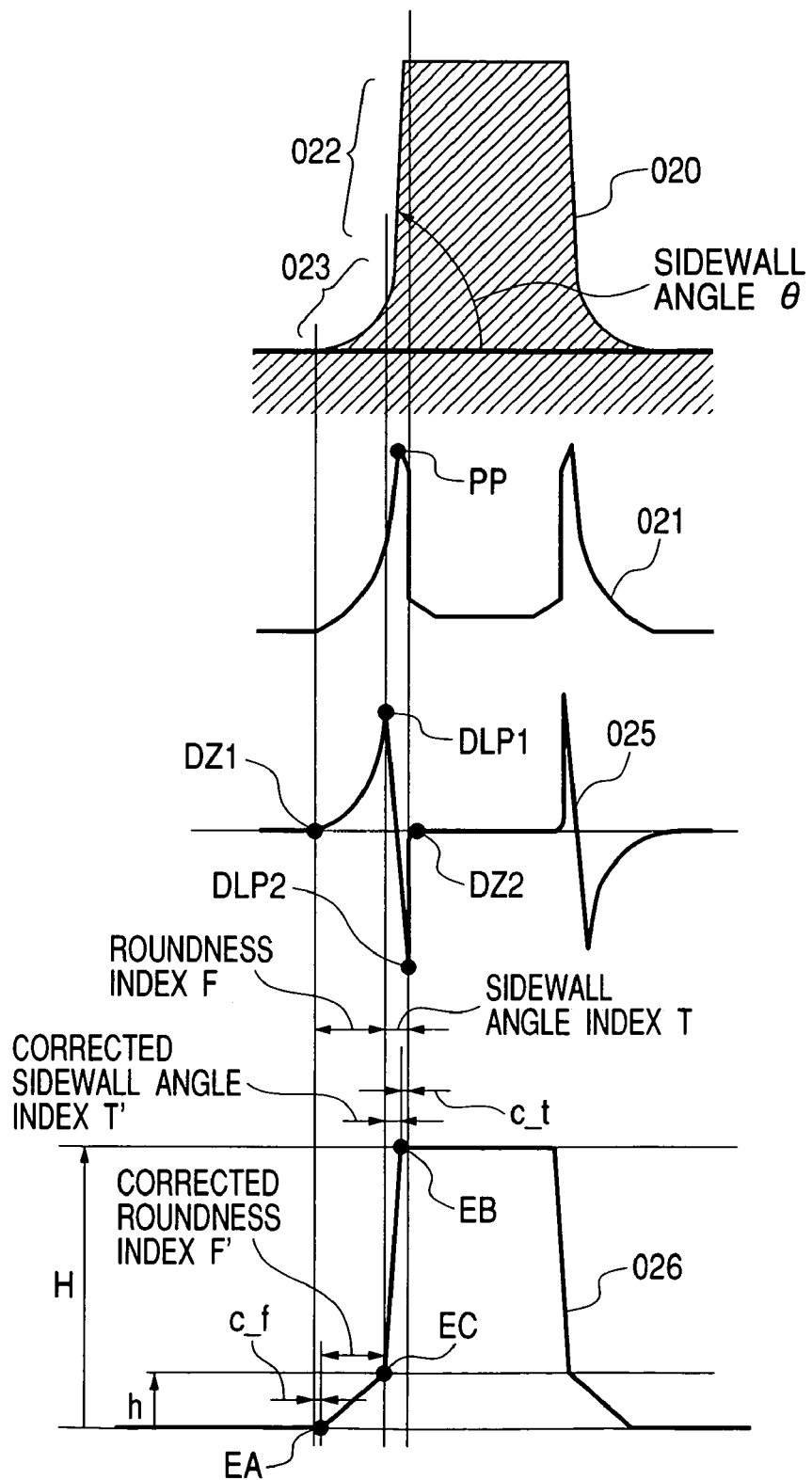
FIG. 10 illustrates a method of computing three-dimensional shape indexes, according to the first embodiment of the present invention.

FIG. 6 is a conceptual diagram of a procedure of determining etching conditions by use of a pattern shape evaluation system built up on a length measuring SEM 200 (schematic constitution is shown in FIG. 10), according to a first embodiment of the present invention. In this embodiment, first, a pattern is formed by an etching treatment comprised of a BARC etch (step 1001), a poly Si etch (1) (step 1002) and a poly Si etch (2) (step 1003) under appropriate initial conditions, and a photoresist removing treatment (1004) comprised of photoresist ashing and cleaning. Here, steps 1001 to 1003 are carried out continuously in the same etcher 600. Next, by use of the length measuring SEM 200, an electron beam image of the circuit pattern after etching is picked up (step 1005), thereafter the shape of the pattern is evaluated by use of the electron beam image (step 1006), and the results thus obtained are displayed on a screen (step 1007). Based on the evaluation results obtained, the operator evaluates the acceptability of the pattern shape, then determines the step or steps of which the process conditions are to be modified and sets new conditions (steps 1008, 1009). The method of picking up sectional shape data will be separately detailed later.

Figure 7:
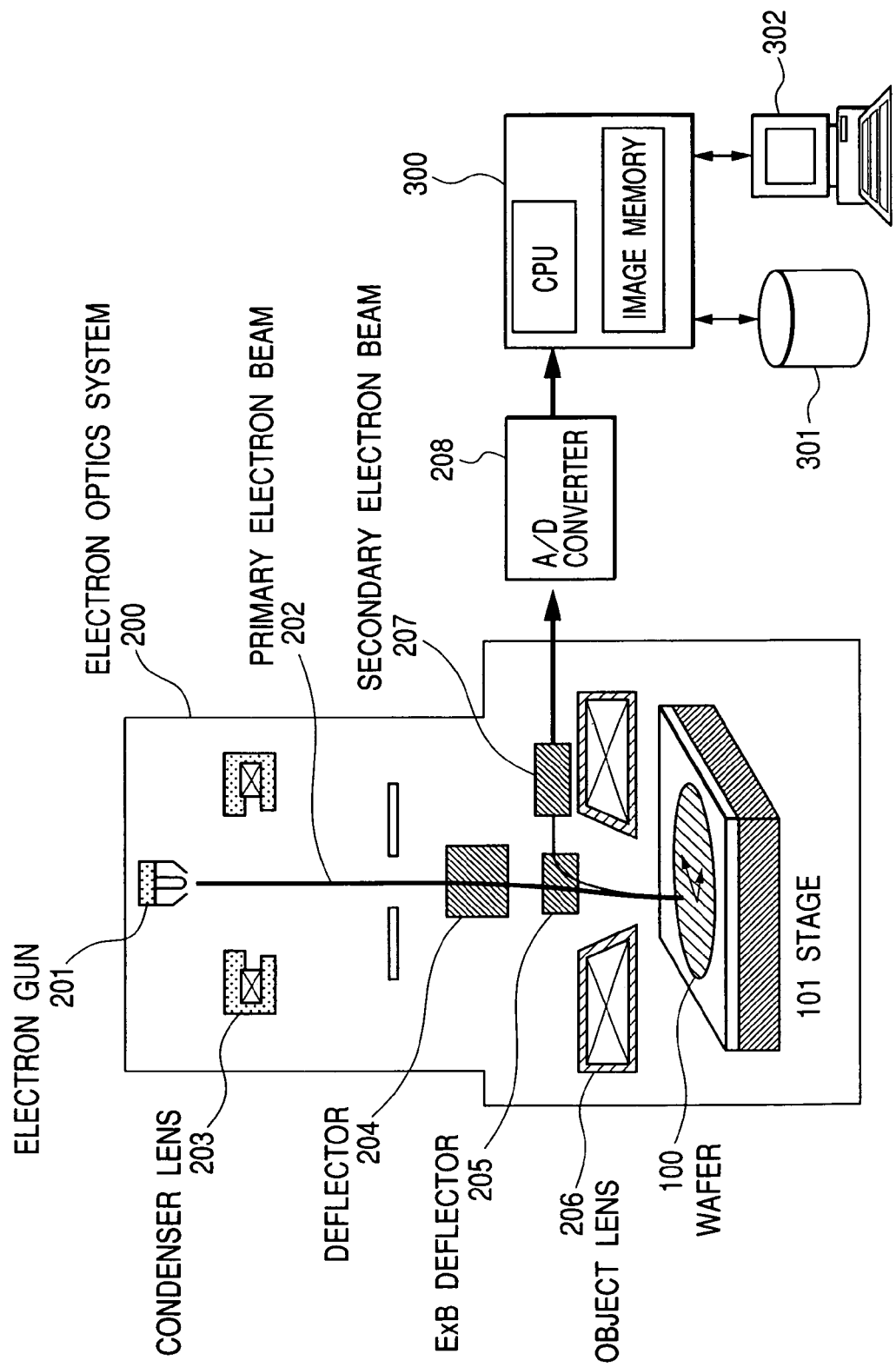
FIG. 7 shows the overall constitution of a CD-SEM pertaining to the first embodiment of the present invention.

FIG. 7 is a block diagram showing the constitution of the length measuring SEM 200 used in the present pattern shape evaluation system. In FIG. 7, a primary electron beam 202 emitted from an electron gun 201 is condensed by a condenser lens 203, is then led through a beam deflector 204, an ExB filter 205 and an objective lens 206, and is focused onto a wafer 100 placed on a stage 101. When the wafer 100 is thus irradiated with the electron beam, secondary electrons are generated from the wafer 100. The secondary electrons generated from the wafer 100 are deflected by the ExB 205, and are detected by a secondary electron detector 207. A two-dimensional electron beam image is obtained by detecting electrons generated from the specimen synchronously with two-dimensional scanning of the electron beam by the deflector 204, or with a repeated scanning in X direction of the electron beam by the deflector 204 and a continuous movement in Y direction of the wafer 100 by the stage 101.

The signal detected by the secondary electron detector 207 is converted by an A/D converter 208 into a digital signal, which is fed to an image processing unit 300. The image processing unit 300 comprises an image memory for temporarily storing a digital image, and a CPU for computing a line profile and feature indexes from the image on the image memory. Further, a storage medium 301 is provided for storing the detected image or line profile or the computed pattern shape data and the like. A display unit 302 is connected to the image processing unit 300 so that required operations of apparatuses, confirmation of the detection results and the like can be realized through a graphical user interface (hereinafter referred to as GUI).

Next, the procedure of computation of three-dimensional shape data conducted by the image processing unit 300 will be described referring to FIGS. 8 to 11.

Figure 8:
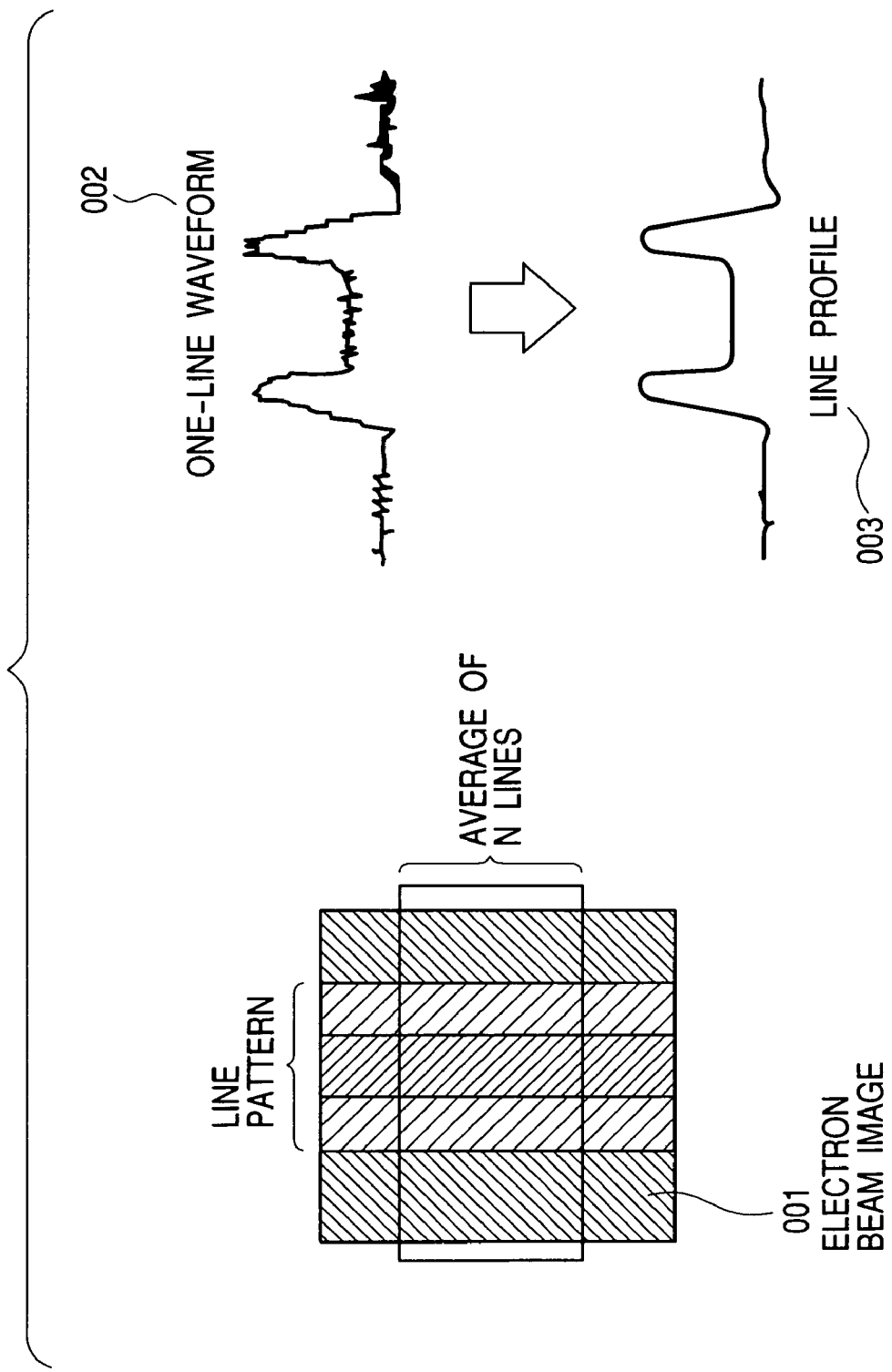
FIG. 8 illustrates a line profile treatment according to the first embodiment of the present invention.

First, as shown in FIG. 8, in order to improve S/N, waveforms 002 of individual lines in an electron beam image 001 obtained are averaged for N lines, to produce a smooth line profile 003. The line profile 003 shows a signal quantity according to the shape of a sidewall of the pattern. The details of the relationship between the signal quantity and the pattern sectional shape will be described by using FIGS. 9A and 9B.

Figure 4:
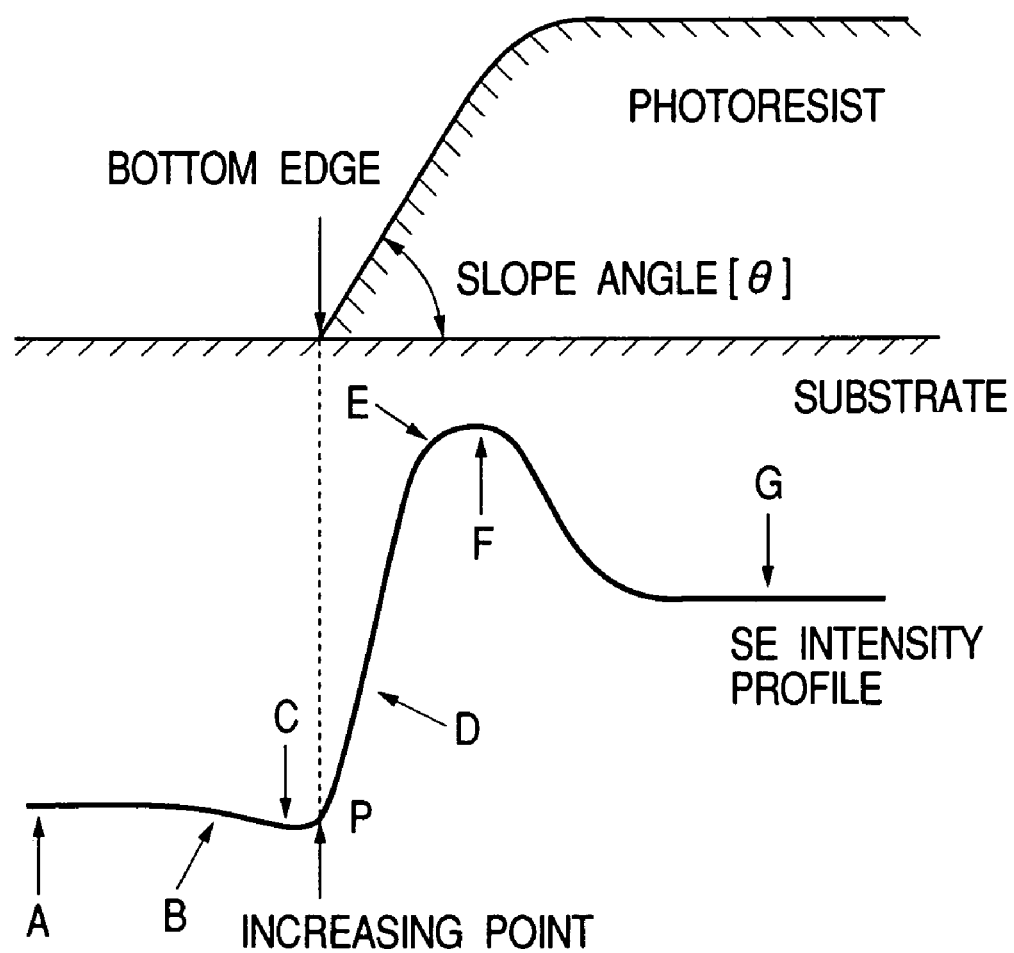
FIG. 4 is a schematic diagram showing the relationship between the sectional shape of a photoresist and the intensity of a secondary electron signal.

As has been described referring to FIG. 4, the signal quantity varies according to the sidewall angle, and the secondary electron signal quantity shows a maximum in the vicinity of a position shifted by one half of the beam diameter from the top edge of the pattern. As for the relationship between the signal quantity of the pattern sidewall portion and the slope angle θ, it is known that the secondary electron signal quantity increases in proportion to 1/cos θ. Therefore, where the sectional shape 110 is free of bottom corner roundness and the sidewall as a whole maintains a comparatively high slope angle, as shown in FIG. 9A, the line profile 011 increases rapidly from the bottom edge; on the other hand, where the sectional shape 020 has a rounded bottom corner, as shown in FIG. 9B, the secondary electron signal quantity at the rounded bottom corner portion 023 is smaller than that at an upper portion 022 having a comparatively higher slope angle.

By utilizing this, sectional shape data are obtained by the following procedure.

First, by separating a smaller signal quantity portion and a larger signal quantity portion from each other, the higher slope angle portion 022 and the rounded bottom corner portion 023 are separated from each other by use of only an SEM image obtained by observation of the specimen from the upper side.

Figure 9A:
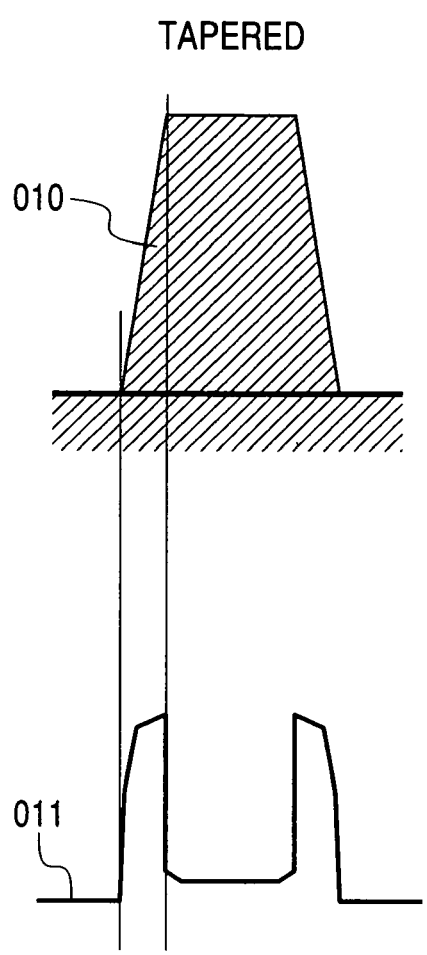
FIGS. 9A and 9B are diagrams for illustrating the difference in the line profile of an SEM image due to a difference in sectional shape.
Figure 9B:
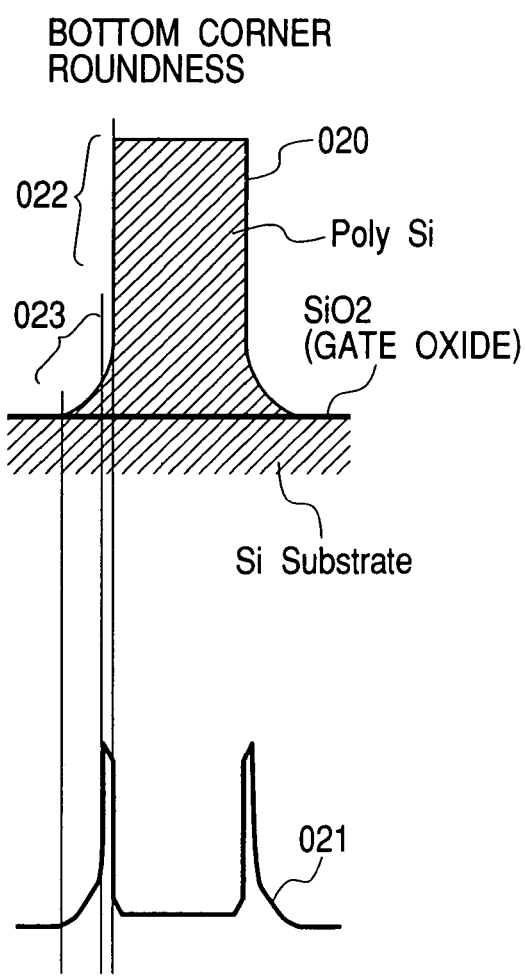
Figure 11:
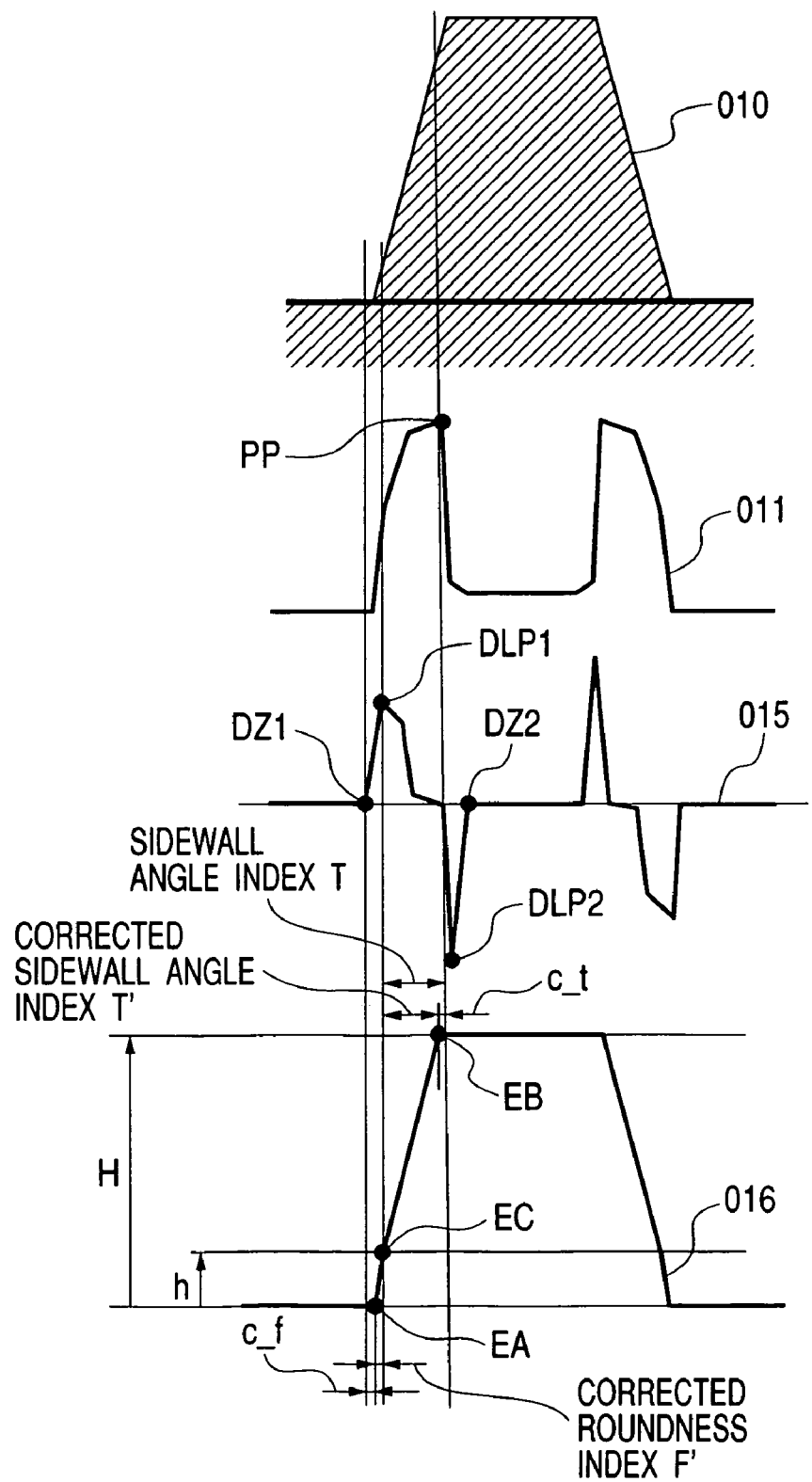
FIG. 11 illustrates a method of computing the three-dimensional shape indexes, according to the first embodiment of the present invention.

FIG. 10 is a detailed illustration of FIG. 9B, and FIG. 11 is a detailed illustration of FIG. 9A.

As shown in FIG. 10, when a differential waveform 025 of the obtained line profile 021 is formed, the resulting waveform has extremal values (DLP1, DLP2) at positions where the original line profile 21 shows a rapid change in lightness. Therefore, the portion between these extremal values DLP1 and DLP2 is associated with a comparatively higher slope angle portion 022 of the sidewall. Accordingly, the distance between the extremal values is made to be a sidewall angle index T.

On the other hand, the portion ranging from the extremal value (DLP1) on the outside of the differential waveform of the edge portion to the point (DZ1) where the differential waveform takes a value of zero, i.e., to the point where the lightness is the same as that of the substrate, represents the rounded bottom corner portion having a comparatively lower sidewall angle; accordingly, the distance between DLP1 and DZ1 is made to be a bottom corner roundness index F. Similarly, the results of obtainment of indexes as to the waveform of FIG. 9A are shown in FIG. 11.

As is seen from comparison of FIG. 10 with FIG. 11, the sidewall angle index T is proportional to tan(π−θ) if the pattern height H is constant, and the value thereof decreases as θ approaches a rectangle. In the case of a retrograde, data on the sidewall portion are lost, and only the portion due to an edge effect is detected, so that the sidewall angle index T remains at a constant value. In contrast, the bottom corner roundness index F increases as the bottom corner roundness increases. Thus, with these indexes, it is possible to obtain three-dimensional shape data on the pattern which are particularly important in the etching step.

In addition, by utilizing these indexes, it is also possible to estimate the outline of the pattern sectional shape. First, the above-mentioned T and F are corrected as follows, taking into account the edge effect and the resolution of the SEM images.

$$T' = T - c\_t \quad \text{(Formula 1)}$$

$$F' = F - c\_f \quad \text{(Formula 2)}$$

In Formula 1, c_t and c_f are constants. c_t is the width of the edge portion which is observed even where the pattern is perfectly perpendicular. This is a value determined principally by the edge effect at the pattern top, and may preliminarily be measured for an appropriate sample. c_f in Formula 2 is an offset component which is observed even where the bottom corner roundness is utterly absent. This depends principally on the resolution of the SEM images, such as the beam diameter of the primary electron beam, the distribution of secondary electrons generated inside the object matter, etc.

By use of T' and F', and with the peak DLP1 on the outside of the primary differential as a reference, a point EA with outside F' and zero height (the same height as the substrate) and a point EB with inside T' and height H (the same height as the upper surface of the film under processing) are determined. The film thickness H of the film which is the object of etching is controlled with high accuracy by use of a film thickness meter or the like in the ordinary production line, so that H can be treated as a known value. As the value of H, the result of actual measurement of the film thickness of the object wafer may be used, or a specification value at the time of deposition may be used.

Next, by presuming an appropriate height h, a point EC with the height h is determined at the position of the reference point (DLP1). By connecting these points EA, EB and EC, it is possible to estimate a rough pattern sectional shape, as shown in FIGS. 10 and 11. Here, h is a height corresponding to the location of changeover of etching conditions above-mentioned referring to FIGS. 3A to 3E, and may preliminarily be roughly found from the etch rate in each step and the process time set in the recipe or the like; however, the value of h at this stage may not necessarily be very accurate. Even if the accurate height h of the point EC is unknown, it is possible to obtain sufficient data for determining the questionable step and for coping therewith.

Figure 5A:
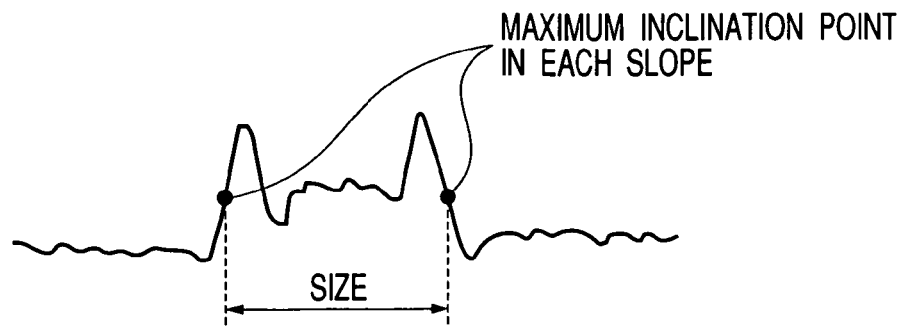
FIGS. 5A to 5C illustrate methods for detecting edges of a line profile.
Figure 5B:
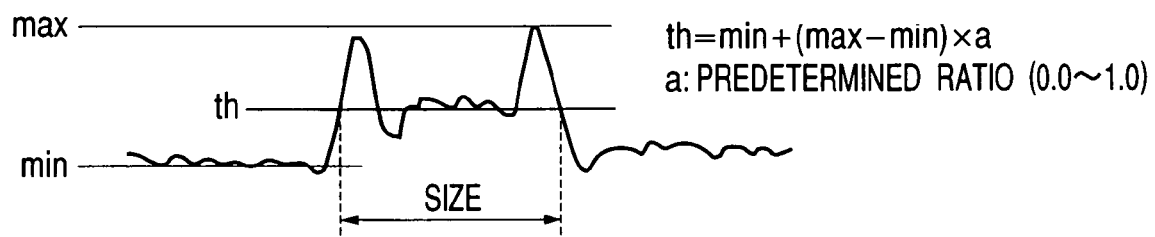
Figure 5C:
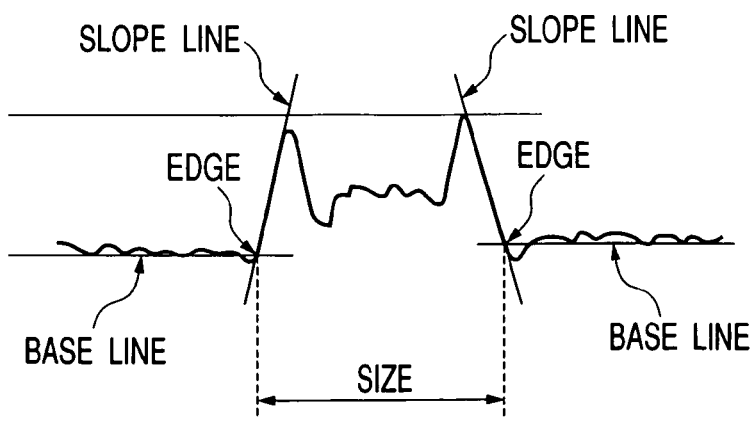

In the conventional length measuring systems shown in FIGS. 5A to 5C, it has been impossible to determine of what point on the pattern the width is being measured. In contrast, when the point EB shown in FIG. 10 or 11 is determined for both left and right edges and the distance between the points EB is determined, the width of the top can be roughly obtained. Similarly, the width of the bottom can be roughly obtained by use of the point EA, and the width of the bottom of taper exclusive of the rounded bottom corner can be roughly obtained by use of the point EC.

Thus, by use of the system according to the present invention, the pattern sizes at desired locations can be measured with high accuracy. With the wiring width measured accurately, it is possible to accurately grasp the size conversion difference from the developed photoresist pattern which has been preliminarily measured.

Where etching is carried out by the steps shown in FIGS. 3A to 3E, the size conversion difference from the size of the photoresist pattern to the top size after the etching is in many cases conditioned by the BARC etch (because generally the BARC film is made of an organic material similar to that of the photoresist and, therefore, the photoresist can be etched at the time of the BARC etch).

Therefore, when the size of the top can be measured accurately, it is also possible to rationalize the BARC etch conditions.

Figure 2A:
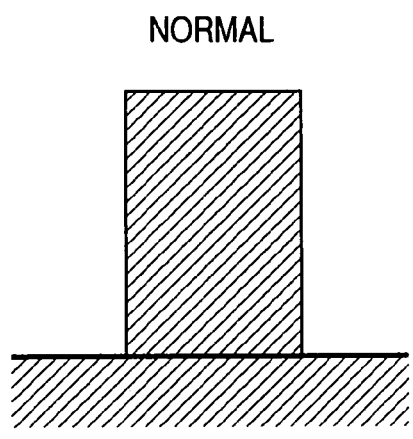
FIGS. 2A to 2D illustrate the shape and abnormal shapes of the pattern to be formed in the etching step.
Figure 2B:
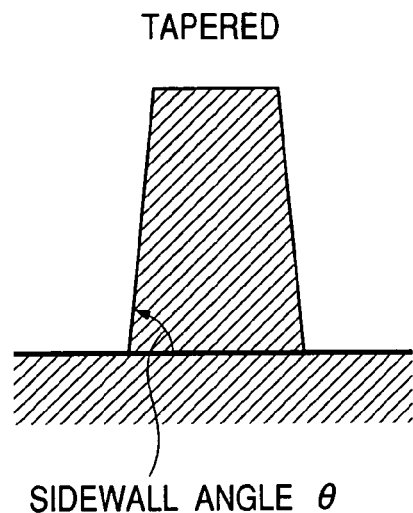

Thus, when the rough pattern shape is found, it is possible for the staff to efficiently set the etching conditions for realizing the desired shape as shown in FIG. 2A. As three-dimensional shape data to be used for determining the etching conditions, other than the estimated shapes 026 and 016 shown in FIG. 10 or 11, the bottom corner roundness index T (or T'), the sidewall angle index F (or F'), the top and bottom pattern sizes and the like may be used as they are, or the result of computation of the sidewall angle θ from the sidewall angle index T may be used.

Where the association between the pattern sectional shape represented by the individual indexes and the individual etching steps shown in FIGS. 3A to 3E is established, it suffices to modify only the conditions of the corresponding step or steps so that the index or indexes will have values representing the desired shape.

Incidentally, the sidewall angle θ can be obtained by the following formula (Formula 3):

$$\theta = \pi/2 - a\tan(T'/H) \quad \text{(Formula 3)}$$

While the signal waveform has been divided into a higher slope angle portion and a lower slope angle portion by use of values of the primary differential in the above embodiment, the same or similar results can be obtained also by dividing a profile waveform into regions based on the signal quantity itself by use of an appropriate threshold.

Next, the locations for pattern shape evaluation after etching will be described referring to FIGS. 12A and 12B. In the etcher, it is in many cases impossible to obtain a uniform etching performance for various positions on the wafer, due to the influences of plasma density distribution in the process chamber or the like. Therefore, uniformity in the wafer surface is also an important item in determination of etching conditions.

Figure 12A:
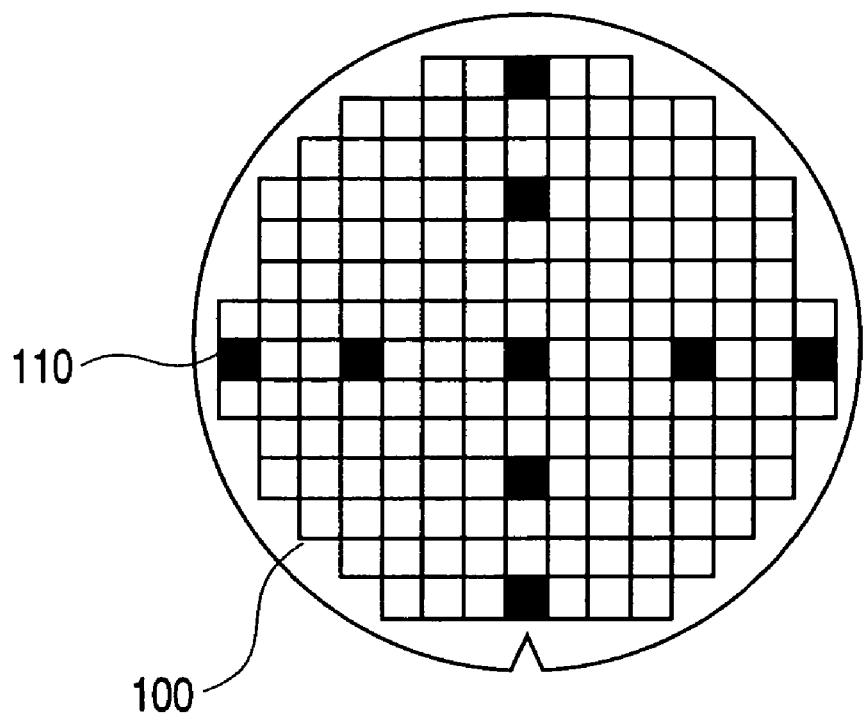
FIG. 12A illustrates locations of obtaining the three-dimensional shape indexes.

In view of this, it is effective to measure the pattern shape data at several points in the surface of the wafer 100 by the above-mentioned method, as shown in FIG. 12A, and to display variations of the data in an easily understandable form. FIG. 12A shows one example of evaluation positions in the wafer surface. For example, when the shape evaluation is carried out at evaluation object chips 110 represented by solid squares (nine chips in FIG. 12A), it is possible to know the shape distribution in the wafer surface.

In an etching step, the etched state will often varies in a pattern of concentric circles in the wafer surface. Therefore, when a shape index (for example, sidewall angle index T) according to the distance from the wafer center is displayed in a graph as shown in FIG. 12B, the state of the treated wafer can be easily confirmed. Similarly, since the shape varies also under the influence of pattern density or the like, shape index measurement may be carried out at several locations in the chip and position dependency in the chip may be displayed.

Next, an embodiment of displaying the shape evaluation results, for confirming the results, will be described. FIG. 13 illustrates one example in which shape variations in the wafer surface are displayed by use of estimated sectional shapes. The chips for which shape evaluation has been carried out by picking up the images thereof are displayed on a wafer map 120, and estimated sectional shapes 121 and three-dimensional shape indexes 122 associated with the individual chips are displayed. In this case, it is further preferable that the order of presentation of the results can be rearranged according to the chip No., the distance from the wafer center, etc.

Figure 12B:
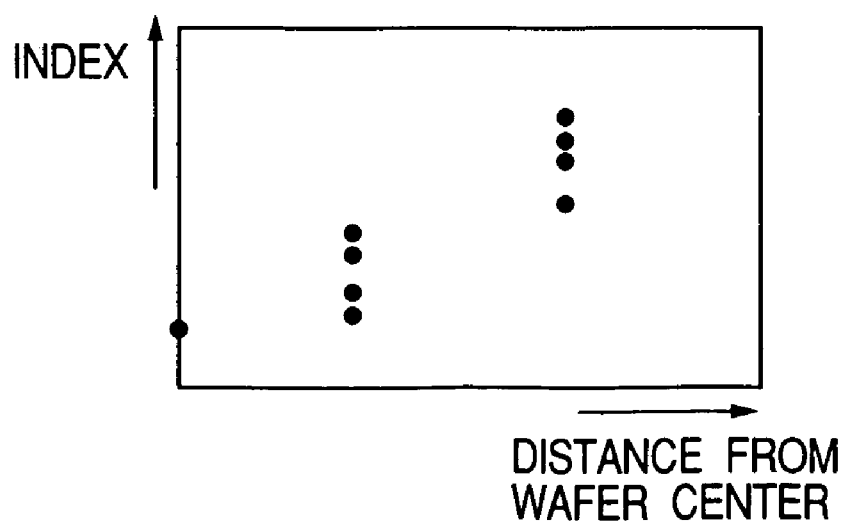
FIG. 12B illustrates a method of displaying the position dependence of the three-dimensional shape indexes, in the first embodiment of the present invention.

In addition, as shown in FIG. 12B, a graph representing the relationship between an index and the position in the wafer surface may be displayed for each index. Further, it is preferable to also display process conditions 123 for the object wafer on the screen.

Figure 14A:
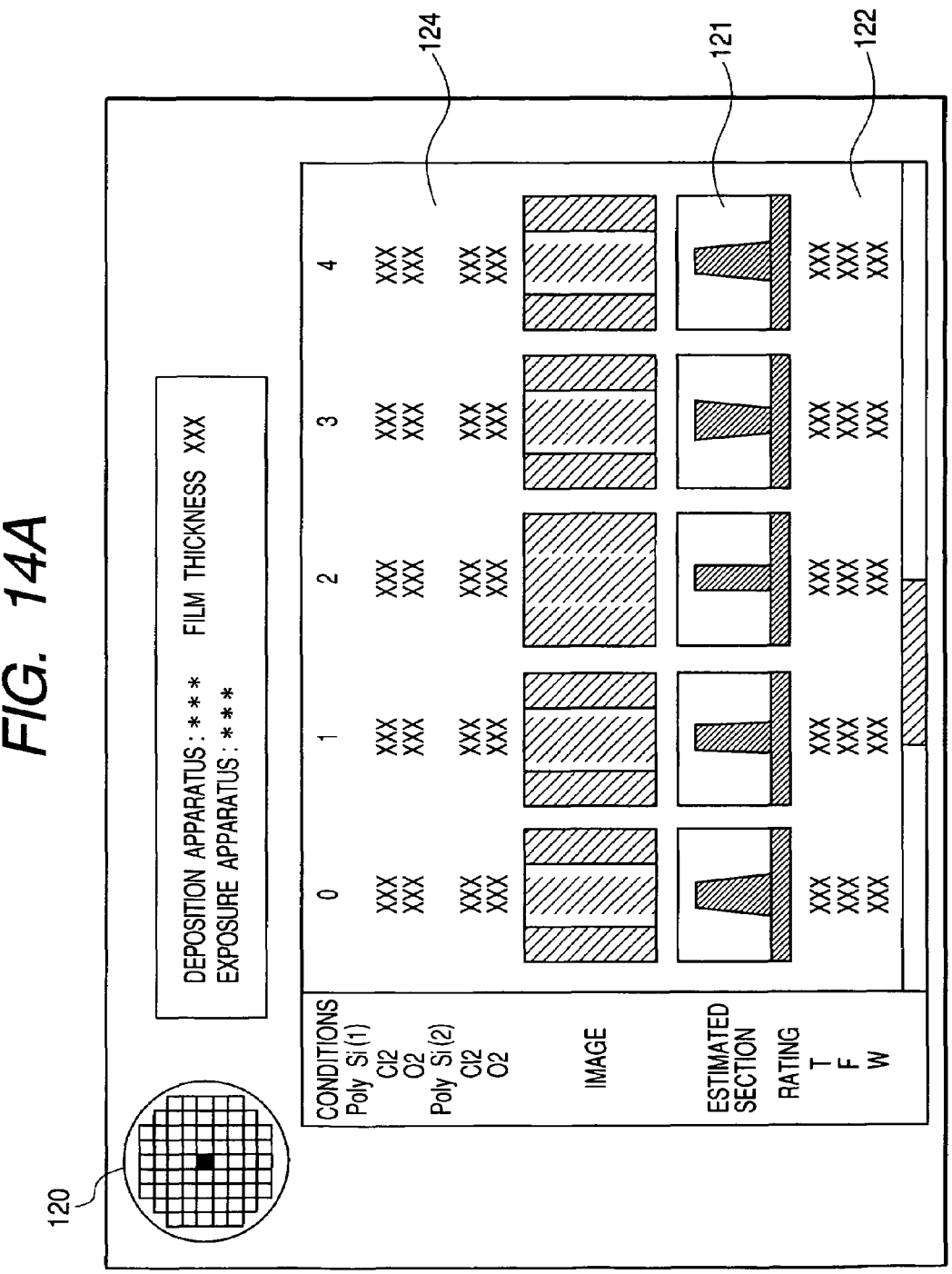
FIG. 14A illustrates a method of displaying the results of obtainment of three-dimensional shape data on a plurality of wafers.

Besides, in determination of process conditions, a plurality of wafers are processed, and a processed-shape comparison is conducted between the wafers. In this case, it is effective to display estimated sectional shapes of the individual wafers together with and in alignment with the process conditions thereof, as shown in FIG. 14A. In FIG. 14A, the pattern evaluation results for the chip position on the wafer map 120 at the top left, of the wafers differing in etching conditions, are displayed in an arrayed form.

In FIG. 14A, the estimated sectional shapes 121 and the three-dimensional shape data 122 are displayed together with the etching conditions 124 for the individual wafers. In this case, if the order of presentation can be rearranged on the basis of a main parameter designated by the user, further effective data can be obtained. In addition, the three-dimensional shape evaluation results associated with the individual parameters (Φx denotes a set of parameters for a certain etching condition) may be presented in the form of a graph, as shown in FIG. 14B, and a graph presentation may be conducted by taking a main parameter on the axis of abscissas, as shown in FIG. 14C.

Figure 14B:
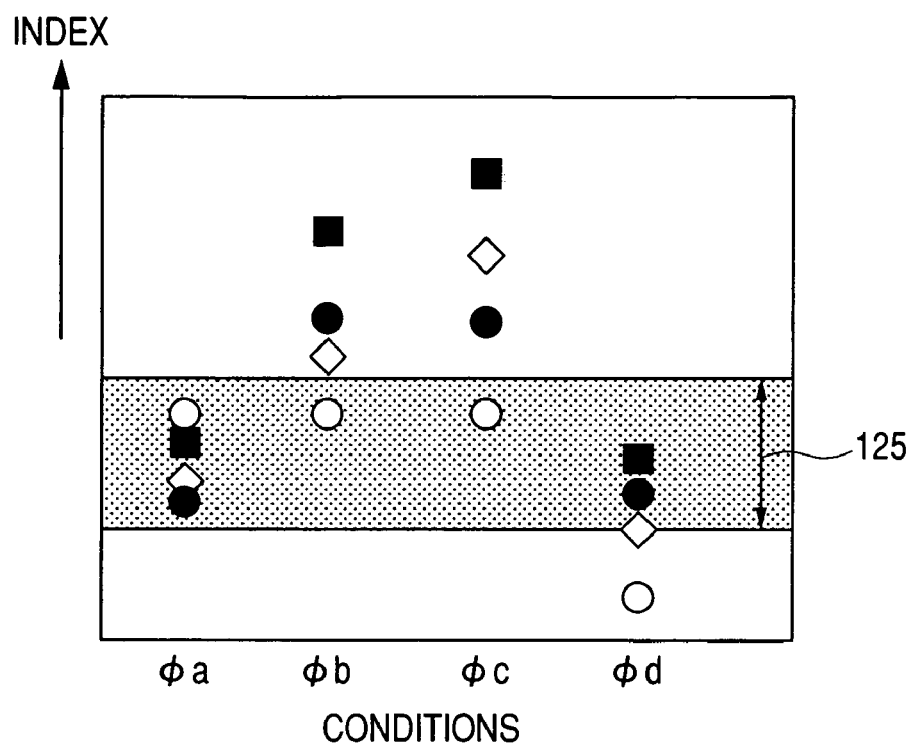
FIG. 14B illustrates a method of displaying wafer dependency.
Figure 14C:
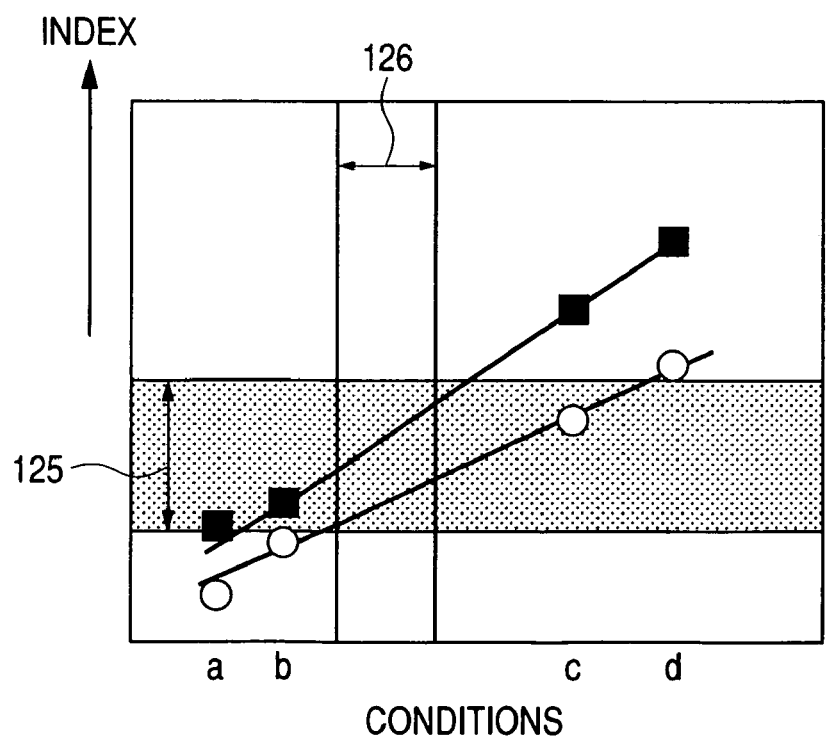
FIG. 14C illustrates a method of displaying etching condition dependency, in the first embodiment of the present invention.

The shaded portions of FIGS. 14B and 14C indicate a target range 125 of three-dimensional shape, and particularly in the case of a presentation as shown in FIG. 14C, it is possible to roughly estimate the etching conditions 126 under which the desired shape can be obtained. In addition, as shown in FIGS. 14B and 14C, for example, a presentation method of using different marks depending on the positions on the wafer is also effective.

Thus, according to the present invention, it is possible to obtain pattern section data easily and at high speed. In particular, it is possible to achieve shape evaluation associated with the etching steps, which could not be achieved by the conventional length measuring system, and, as a result, it is possible to enhance the efficiency of determination of etching conditions.

The section observation conducted in the conventional determination of etching conditions takes a lot of time, and requires the operator to have techniques different from that for handling the etcher, such as preparation of specimens, pickup of sectional SEM photographs, etc. In contrast, the shape evaluation according to the present invention can be automatically conducted by use of an SEM provided in the production line, and can be performed speedily by anyone. In addition, since the measurement can be easily made at many points in the wafer and in each chip, it is possible to easily grasp the shape distribution in the chip and the shape distribution in the wafer surface.

Furthermore, the specimen is not damaged at the time of shape evaluation; therefore, when a good shape is obtained, the wafer under evaluation can be fed to the next processing step.

Besides, in the present invention, the variation in pattern shape due to a modification of process conditions can be evaluated quantitatively. Therefore, it is easy to set process conditions for realizing the desired shape, and it is possible to efficiently optimize the conditions.

Incidentally, while the sidewall angle, the bottom corner roundness and the pattern width have been used as indexes in the above embodiment, when the distance between the inside peak and the zero point is measured, the distance can similarly be used as an index which indicates the roundness of the pattern top. Since the shape to be controlled differs according to each step, these indexes may be used in combination, as required. For example, at the time of Si etching in a device isolation step in which the pattern top is rounded for enhancing the burying property, the top roundness can be used as an effective index.

Next, a second embodiment will be described. While the step for which the conditions are to be manually modified and the amount of process condition modification have been determined from the pattern sectional shape estimated by SEM in the first embodiment, these condition modifications are automatically performed in the second embodiment.

In this embodiment, first, main pattern shape indexes and process condition adjusting parameters for the individual steps corresponding thereto are preliminarily designated. In addition, for the pattern shape indexes, target values and allowable values are preliminarily stored.

A wafer for determination of etching process conditions is etched, the pattern shape obtained is evaluated by use of SEM images, and the pre-designated process condition adjusting parameters are modified based on the differences between the obtained pattern shape and the target values. The processing and the evaluation are repeated until the target shape is obtained.

The procedure of determining process conditions according to the second embodiment of the present invention will be described referring to FIG. 1. In this embodiment, first, a pattern is formed by carrying out an etching process comprised of BARC etch (step 1001), poly Si etch (1) (step 1002) and poly Si etch (2) (step 1003) and a photoresist removing step (1004) comprised of photoresist ashing and cleaning, under appropriate initial conditions. Next, an electron beam image of the etched circuit pattern is picked up by use of a length measuring SEM 200 (step 1005), and then the sectional shape of the pattern is evaluated by use of the electron beam image (step 1006).

The SEM for picking up the electron beam image and the image processing procedure are the same as in the first embodiment above, so that the descriptions thereof are omitted. Based on the shape evaluation results thus obtained, the acceptability of the pattern shape is evaluated according to the difference between each shape index and the target value (step 1010). When a good shape has not been obtained, the step for which the conditions are to be modified is determined and new conditions are set, based on the three-dimensional shape data obtained (step 1011).

Here, the relationship between each shape index and the corresponding step and the target value thereof are obtained by referring to those pre-stored in a storage device (details will be described later). Another wafer is processed under the newly set etching conditions (step 1012), and the evaluation by use of the SEM image and the setting of conditions are repeated, and the procedure is repeated until the target shape is obtained.

Figure 15A:
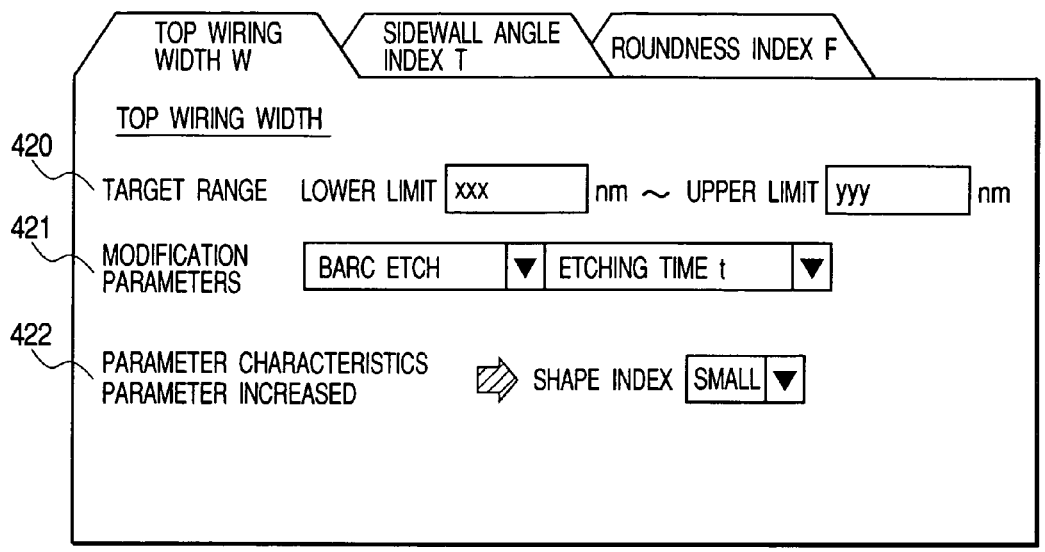
FIG. 15A shows a GUI screen for setting etching condition parameters associated with various shape indexes.

As one example, the case of using the etching time for the BARC etch as a main etching parameter having an influence on the top wiring width will be described. First, the operator sets a main parameter and a target value for controlling the top wiring width W. FIG. 15A shows one example of a setting screen. First, a target range 420 of the top wiring width W is set by use of an upper limit and a lower limit. Next, the etching time for the BARC etch is selected as a modification parameter 421. In this case, parameters modifiable according to each step can be appropriately selected.

Where a qualitative tendency (how the index varies when the parameter is increased) for the selected parameter is already known, the parameter characteristic 422 is preliminarily designated. Other than the data in FIG. 15A, conditions such as the initial values of the etching conditions and the modifiable ranges of the individual parameters are also stored together in the storage device 301. While only the BARC etching time condition is set for the top wiring width in FIG. 15A, shape indexes associated with the desired final shape and the parameters affecting the individual shapes are used appropriately. Naturally, a synergistic effect of a plurality of process parameters on one shape index may be taken into account.

Next, an etching process is carried out under the initial conditions, and the shape indexes measured by use of the SEM image are compared with the target ranges thereof. In this example, the top wiring width is compared with the target values set in FIG. 15A. When the present shape is found to be outside the target range by comparison with the target values, a new condition is set. FIG. 12B illustrates a method for modifying a condition.

Figure 15B:
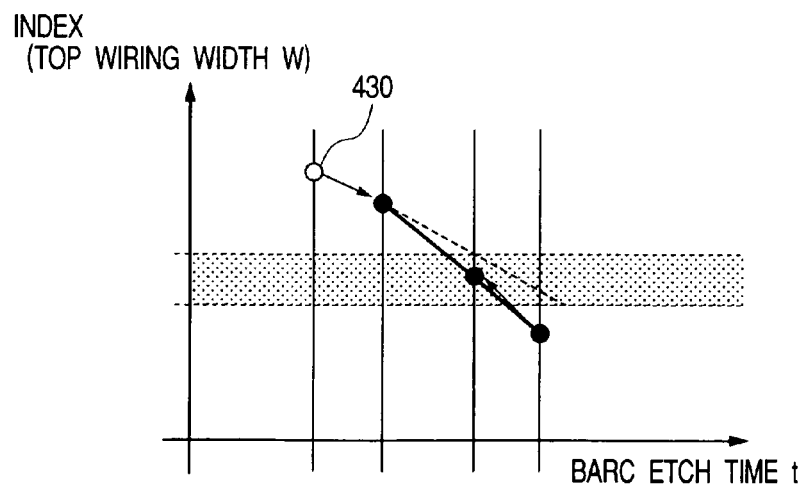
FIG. 15B illustrates a method of setting etching conditions, in a second embodiment of the present invention.

As shown in FIG. 15B, when it is assumed that the initial value 430 of a shape index is greater than the target value, it suffices to set the next process condition at such a value as to reduce the shape index. In this instance, where the parameter characteristic 422 is set in FIG. 15A, the next parameter is set according to the characteristic. In the case of FIGS. 15A and 15B, it is known that the top wiring width W is smaller as the etching time t is longer; therefore, the etching time is set to be longer than the initial condition, and the treatment of the next wafer is conducted.

Here, even if the parameter characteristic 422 is unknown at the time of the first modification of condition, the characteristic becomes clear upon one modification of condition; therefore, there is no particular problem although the number of times of processing is increased by one. Based on the results of the etching process thus conducted, the second and latter modifications of condition are conducted as follows. Where the initial condition is t(0), the top wiring width at that time is W(0), the etching time after the i th modification of condition is t(i), and the top wiring width at that time is W(i), the (i+1)th etching time setpoint t(i+1) can be set by the following formula:

$$t(i+1)=(Wt-W(i))*(t(i)-t(i-1))/(W(i)-W(i-1))+t(i) \qquad \text{(Formula 4)}$$

where Wt is the target value (the average of a lower limit and an upper limit) of the shape index. Thus, the next processing condition is set based on the difference between the shape evaluation result and the target value, and the processing and the evaluation are repeated until the target shape is obtained. While the top wiring width and the etching time have been described referring to FIGS. 15A and 15B above, condition setting can be conducted in the same manner also for other shape indexes and etching conditions.

Thus, in the shape evaluation method according to the present invention, differences in the three-dimensional shape of the pattern can be evaluated quantitatively. Therefore, by preliminarily designating the parameters for controlling the shape according to each shape index, determination of the etching process conditions can be performed automatically.

All of these steps for determining the process conditions may be conducted automatically. Alternatively, automatic setting of a process condition and processing may first be repeated several times, and, based on the results, the staff may determine the detailed conditions. Besides, where the given parameters are inadequate, the processed shapes may not converge into the target range; in such a case, it is recommendable to preliminarily set an upper limit to the number of times of condition modification and to issue an alarm when the upper limit is exceeded.

Here, the etching conditions (ΦBARC, ΦP1, ΦP2) in FIG. 1 represent sets of etching parameters for the individual steps. In addition, the condition determining steps illustrated in FIGS. 15A and 15B are simply expressed by use of the functions f(ΔW, ΔT, ΔF), g(ΔW, ΔT, ΔF), and h(ΔW, ΔT, ΔF) in FIG. 1. While steps 1005 and 1006 are conducted on the SEM 200 in FIG. 1, the other data processing than the image pickup (step 1005) may be conducted on the SEM 200, on the etcher 600, or on a separate computer. These apparatuses are desirably linked to each other through a network.

Thus, in the second embodiment, the parameters can be automatically set, based on the results of quantitative evaluation of the pattern shape. In particular, since the etching conditions are modified based on the shape evaluations associated with the steps of the etching process, it is possible to enhance the efficiency of determining the etching conditions. Therefore, in addition to the common effects shared with the first embodiment, the second embodiment has the merit that the determination of etching conditions can be performed speedily and easily by anyone.

Next, a third embodiment will be described referring to FIGS. 16 and 17. By use of the three-dimensional shape data obtained from an SEM image by the method described in the first and second embodiments above, the states of the process can also be monitored on the production line.

Figure 16:
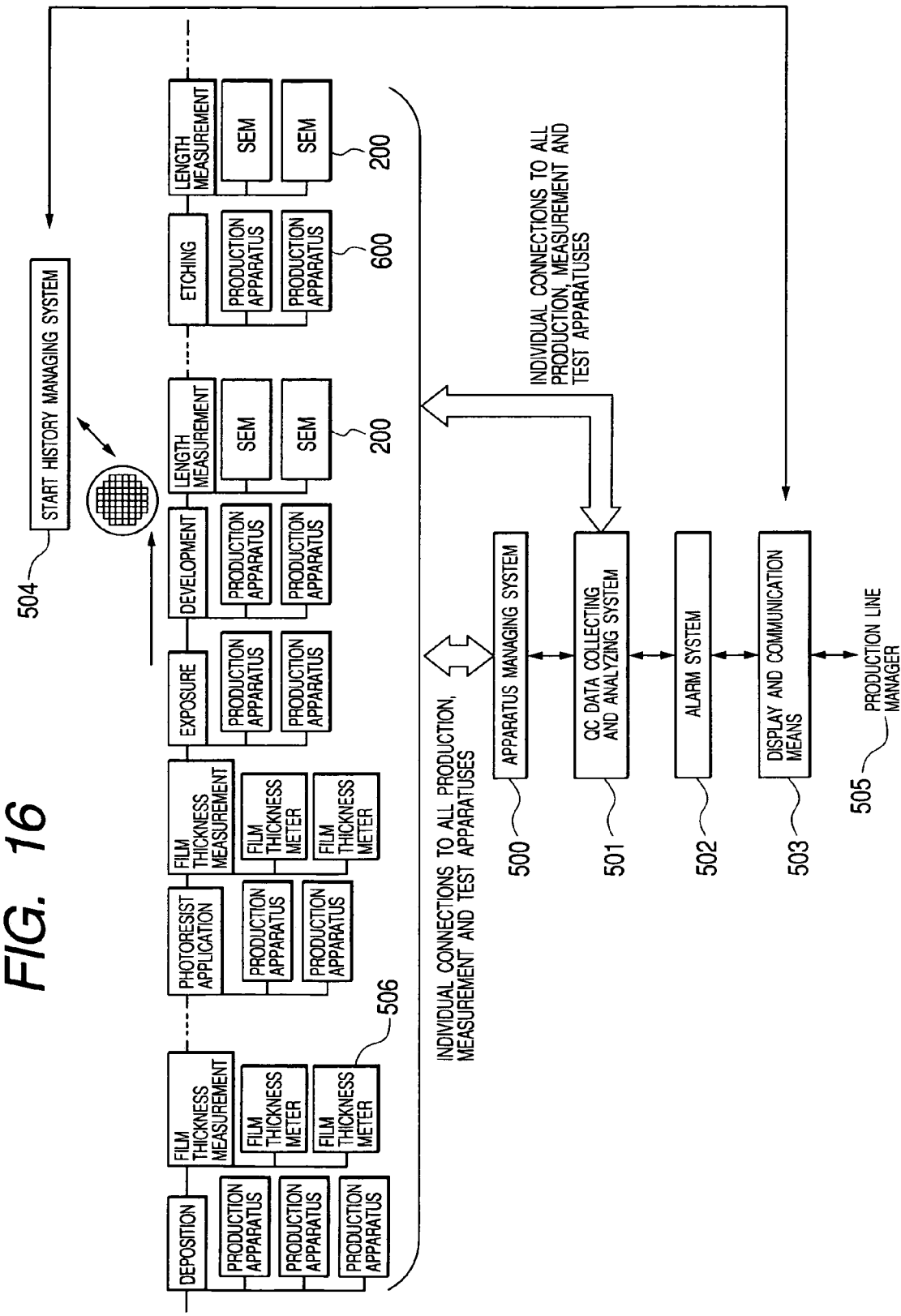
FIG. 16 shows an example of building up a semiconductor manufacturing line according to a third embodiment of the present invention.

FIG. 16 illustrates an example of building up a production line to which the present invention is applied. Each of the production apparatuses is linked to an apparatus managing system 500 through a network. The apparatus managing system 500 manages not only the operating conditions and maintenance conditions of these apparatuses but also such data as production conditions for each kind of product and each step. Besides, measuring instruments such as film thickness meters 506 and length measuring SEMs 200 are linked to a QC data collecting and analyzing system 501, whereby the results of film thickness measurement and length measurement are collected and managed.

In addition, the QC data collecting and analyzing system 501 is linked to an alarm system 502, and when some abnormality is generated in the length measurement results, the situation is reported to a production line manager 505 through a display and communication means 503.

Besides, information about when, which step and on which apparatus the processing of each wafer has been started is managed by a start history managing system 504. Therefore, it is possible to refer to the process histories of all wafers, as required. In such a production line, as the film thickness data for use in estimation of a sectional shape, the present wafer value can be used securely.

Figure 17:
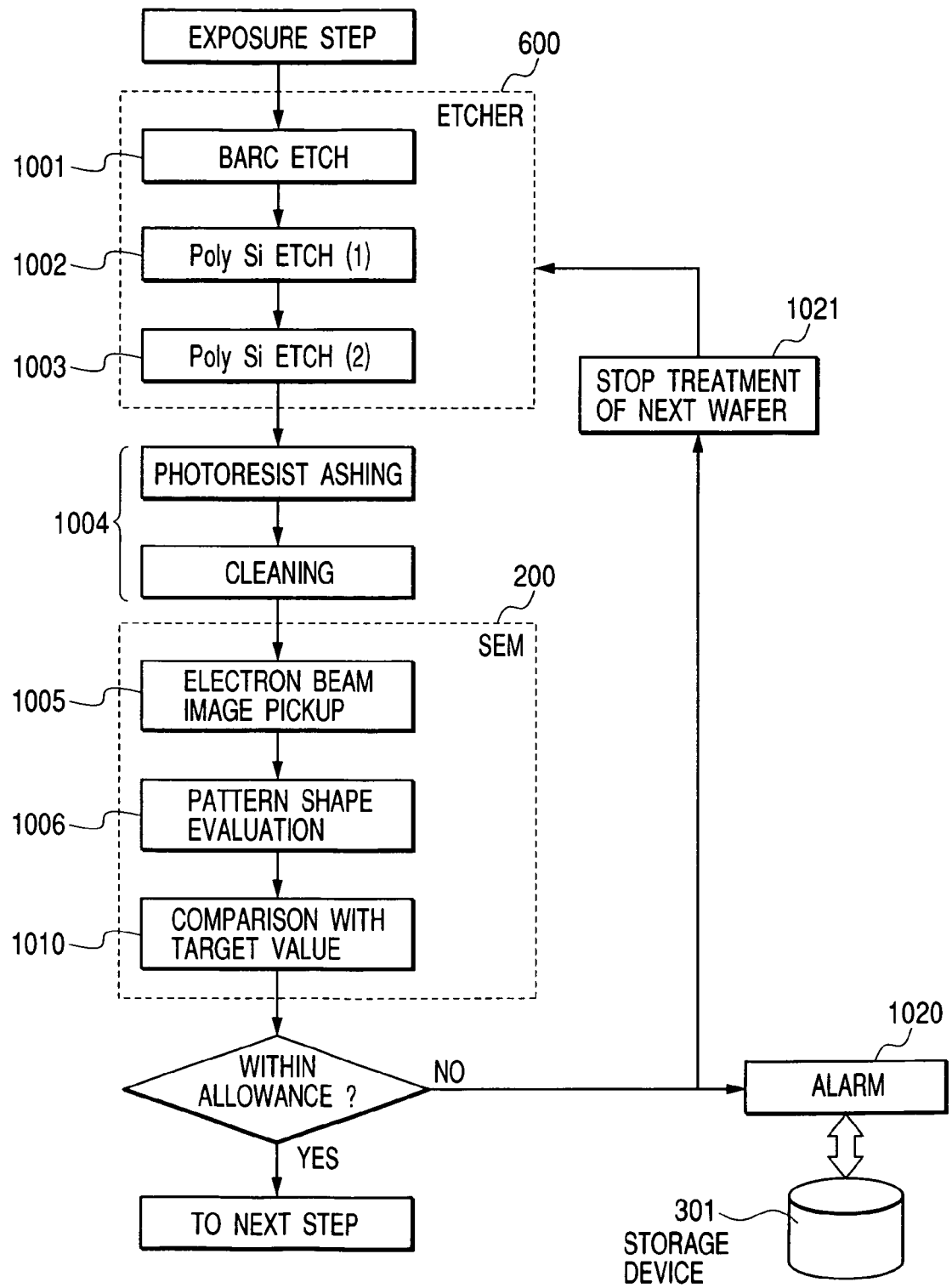
FIG. 17 is a flow sheet of a method of monitoring an etching process in the third embodiment of the present invention.

FIG. 17 illustrates an embodiment of the process of an etching process monitor system according to the present invention. In the line for carrying out the process monitoring, allowable values of pattern shape indexes such as wiring width, sidewall angle, and bottom corner roundness of pattern are preliminarily set. These setpoints are preliminarily recorded in a recording medium 301. In the production line, the pattern on the wafer having been subjected to an etching process (steps 1001 to 1003) and photoresist ashing and cleaning (step 1004) is evaluated by use of an SEM image thereof (steps 1005 and 1006).

The SEM for picking up the electron beam image and the image processing procedure are the same as in the first embodiment above, and the descriptions thereof are therefore omitted. The three-dimensional shape data of the pattern obtained from the SEM image are compared with the target values and the allowable values (step 1010), and when the allowable value or values are exceeded, an alarm is sent to the production line manager through the communication means (503 in FIG. 16) (1020), and the subsequent wafer treatment is stopped (1021). In this case, when the pattern shape exceeding the allowable value and the etching step corresponding thereto are displayed together, it is possible to easily find the step in which the problem has occurred and to swiftly cope with the trouble.

The data on the corresponding etching step may be preliminarily registered and stored in the recording medium, as shown in the second embodiment above. In addition, shape variations in the wafer or in a chip can also be monitored, in the same manner as in the first embodiment above.

The shape evaluation according to the present invention can be automatically conducted by use of the SEM in the production line. Thus, by monitoring the three-dimensional pattern shape through using the shape evaluation system according to the present invention, it is possible to find early the abnormality present in the etching process and to prevent production of unacceptable products.

In particular, it is possible to achieve shape evaluations associated with the steps of the etching process, which has been impossible by the conventional length measuring system, and it is possible to swiftly find the cause of a trouble and, therefore, to enhance the operating efficiency of the etcher. In addition, since the measurement can be easily conducted at many points in the wafer and in a chip, the shape distribution in the wafer and the shape distribution in a chip can also be easily grasped.

Next, a fourth embodiment will be described referring to FIG. 18. In the first and second embodiments above, the method of obtaining three-dimensional shape data from the SEM image and the method of determining etching conditions based on the three-dimensional shape data thus obtained have been described.

In such a process of determining the etching conditions, data on the relationships between the etching condition and the processed shape in each step, such as that shown in FIG. 15B, can be collected. When the data on the relationships between the etching condition and the processed shape are preliminarily recorded as a data base, it is possible to constantly maintain a favorable processed pattern shape by modifying the process condition parameters according to variations in the etching conditions, after the production is started.

Figure 18:
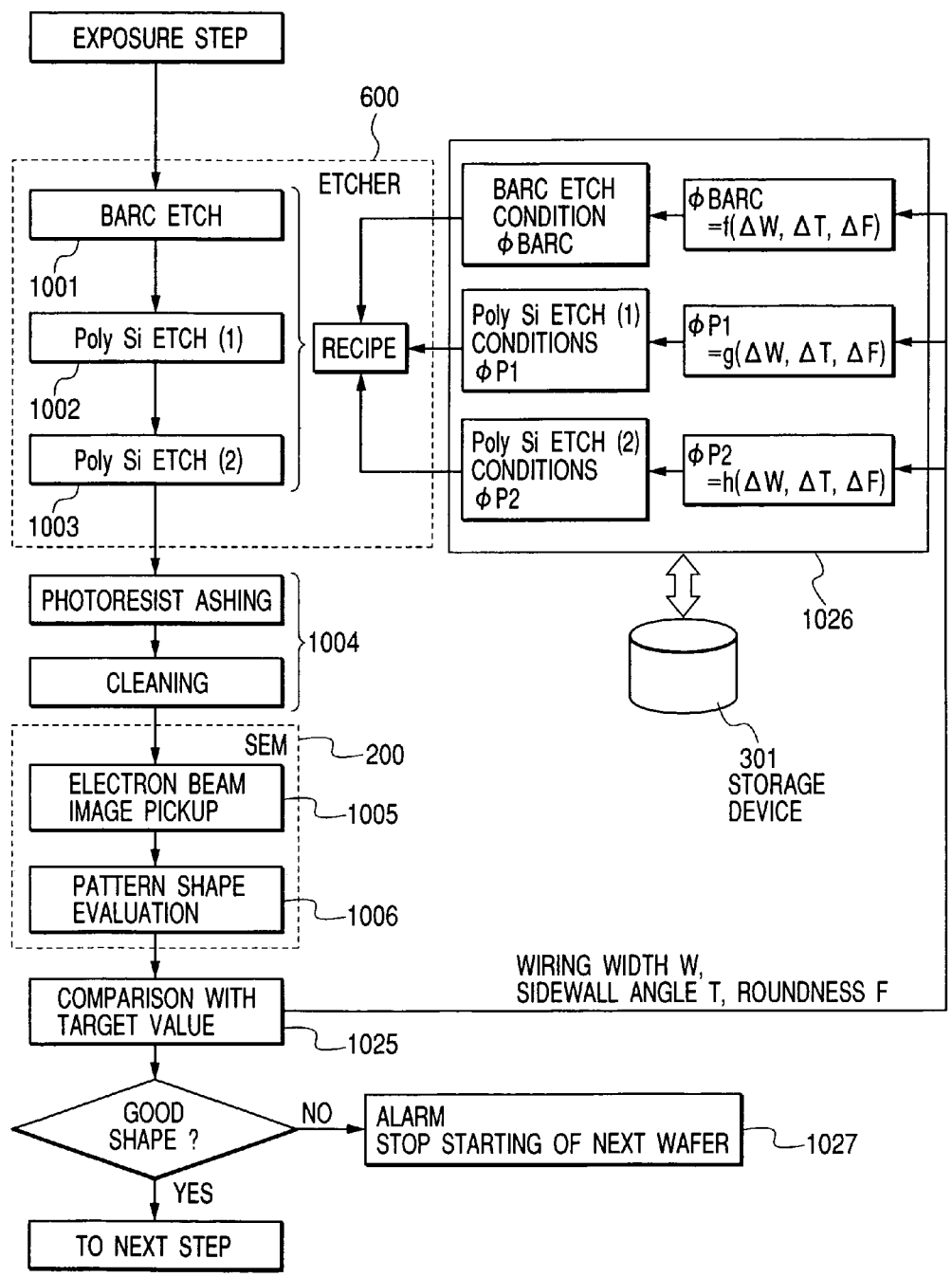
FIG. 18 is a flow sheet of a method of controlling the etching process in a fourth embodiment of the present invention.

FIG. 18 shows the flow of an etching process control according to the present invention. In the same manner as in the third embodiment above, a series of etching process (1001 to 1003) and photoresist ashing and cleaning (1004) are conducted on a wafer, and the processed pattern is evaluated by use of an SEM image thereof (1005, 1006).

The three-dimensional shape data thus obtained are compared with target values (1025), and, based on the results, process conditions for correcting the deviations from the desired shape are computed by use of the pre-examined relationships between the etching condition parameters and the pattern shapes (1026). At the time of processing the next wafer, the processing is conducted by use of the thus corrected process conditions. For the latter wafers, also, the series of etching, shape evaluation and process condition correction are repeated, whereby a stable pattern shape can be maintained constantly.

In addition, where an abnormality exceeding an allowable value is detected in the shape evaluation results, an alarm is sent to the production line manager by use of a communication means (503 in FIG. 16) and the subsequent wafer treatment is stopped (1027). In this instance, when the pattern shape index having exceeded the allowable value and the corresponding etching step are displayed together, it is possible to find the step in which the problem has occurred and to swiftly cope with the trouble.

Figure 19:
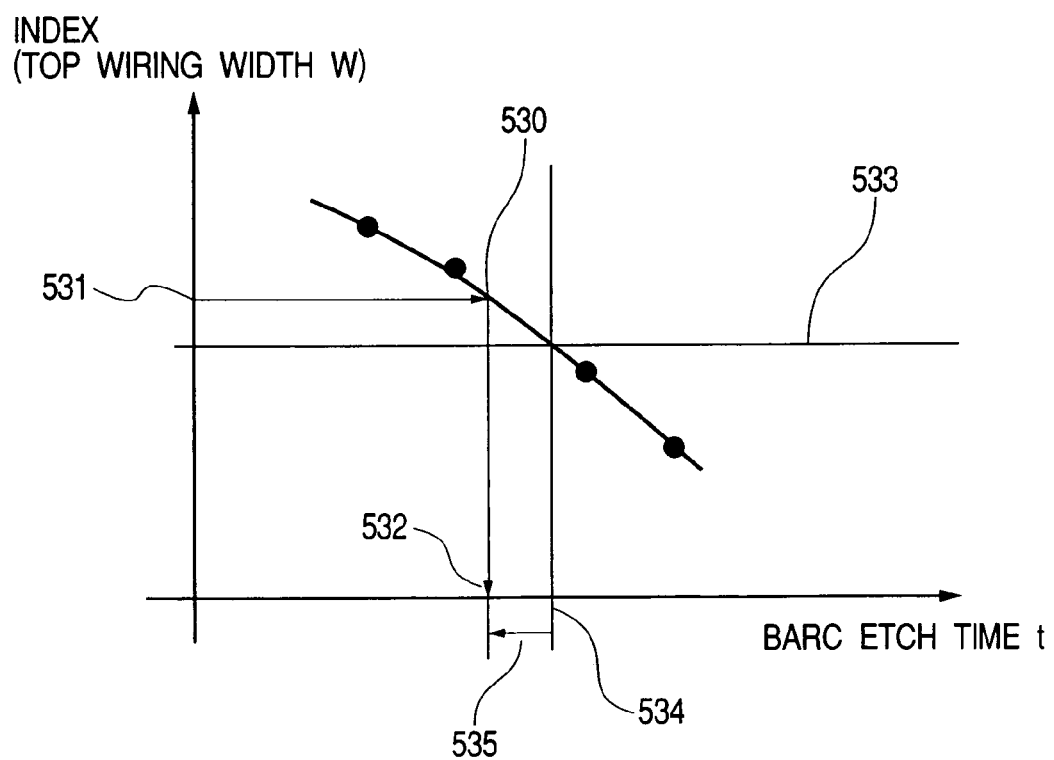
FIG. 19 illustrates a method of computing an etching condition modification amount in the fourth embodiment of the present invention.

When an etching process model is preliminarily constructed by a method in which the data representing the relationship between a process condition parameter and a pattern shape obtained at the time of determining the process conditions are put into an appropriate function 530, as shown in FIG. 19, an appropriate process condition correction amount can be easily computed. To be more specific, by use of the function 530, the difference between the process condition 532 associated with the process shape index 531 of the present wafer and the process condition 534 associated with a target value 533 is made to be the correction amount 535.

While the relationship between BARC etch time and top wiring width is illustrated in FIG. 19, the same method may be applied also to other parameters.

Figure 20A:
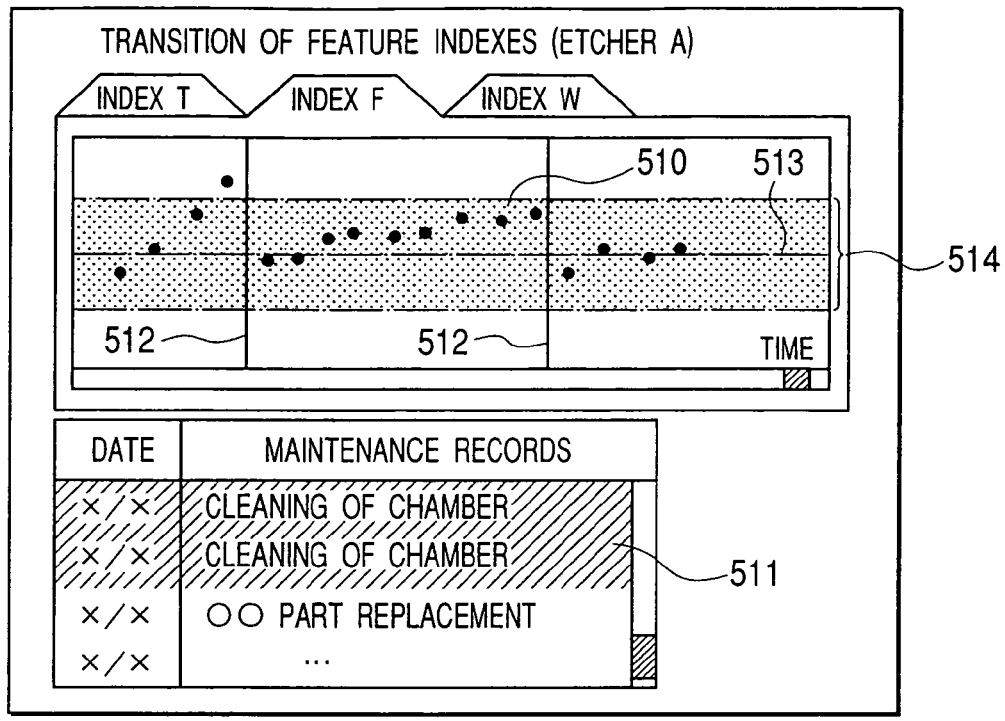
FIGS. 20A and 20B illustrate methods of displaying the conditions of the etching process in the fourth embodiment of the present invention.
Figure 20B:
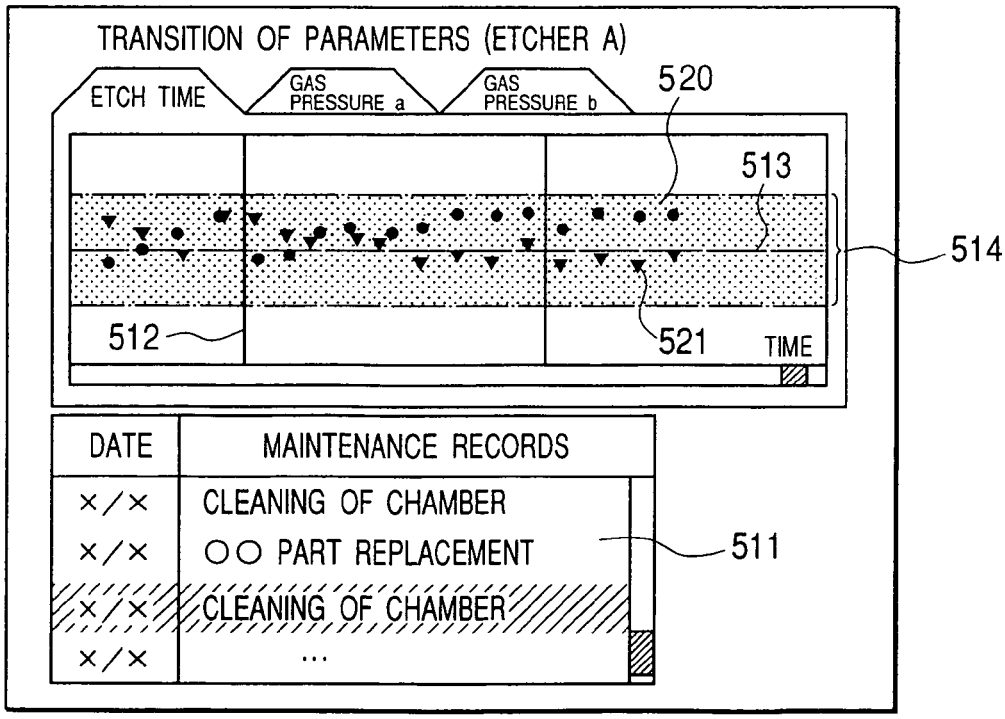

FIGS. 20A and 20B illustrate one examplar embodiment of displaying the data on the etching process obtained, in the process control illustrated in FIG. 18. In the etcher, cleaning and part replacement are periodically conducted, since the pattern shape varies due to the deposition of by-products generated during processing to the inside of the chamber, wearing of parts, and the like.

According to the present invention, maintenance records of these apparatuses and transition of three-dimensional data obtained from the SEM images are displayed together. As shown in FIG. 20A, time series data 510 are presented in a graph on a three-dimensional shape index basis, and, simultaneously, a table of the maintenance records 511 is displayed. The maintenance records in the graph presentation are displayed in different colors, and a maintenance record presentation 512 is displayed also on the graph so that the corresponding time is seen. Incidentally, a target value 513 and an allowable range 514 are displayed together in the time series data graph.

These displays are conducted on an etcher basis. Where data on the same etcher are present on different length measuring SEMs which are linked to one another through a network as shown in FIG. 16, the data may be transferred and displayed. In addition, a reference data base may not necessarily be present on the SEM, and may be present in other location which is connected to the SEM through the network.

The axis of abscissas represents a quantity associated with the order of start of processing on the etcher, such as the day of start of processing of the wafer, the cumulative operating time of the etcher, the cumulative number of wafers for which the processing has been started on the etcher, etc.

While the data are presented on a three-dimensional shape index basis in FIG. 20A, a plurality of three-dimensional shape indexes may be simultaneously displayed on a single graph, or may be displayed through conversion of the data into values indicating the overall conditions, such as sums thereof.

Besides, while the data are presented in a three-dimensional shape index basis in FIG. 20A, naturally, variations in etching parameters estimated from the feature indexes obtained may be displayed, as shown in FIG. 20B.

In the example of FIG. 20B, regulation amounts 521 of etching conditions are displayed together with variations 520 of the etching conditions. By this, it is possible to check the degree of condition modification being conducted and to easily check the degree of variation which cannot be coped with by a condition modification. In addition, outputs of various sensors (pressure gauge, etc.) mounted on the etcher may be displayed, together with FIG. 20A or 20B.

These sensor outputs indicate the condition of the etcher at the time of processing the wafer, so that when the sensor outputs are displayed simultaneously with the above-mentioned data, it is possible to easily confirm the influences of condition variations in the etcher on the pattern shape.

The shape evaluation according to the present invention can be automatically conducted by use of the SEM present in the production line. Thus, by detecting variations in the three-dimensional pattern shape through the use of the shape evaluation system according to the present invention and controlling the etching conditions so as to correct the unfavorable variations, it is possible to realize a constantly stable etching process. In particular, there is the merit that it is possible to achieve shape evaluation associated with the steps of the etching process, which has been impossible by the conventional length measuring system, and that a process control can be performed paying attention to the step in which an unfavorable process variation has occurred.

Now, a fifth embodiment will be described referring to FIG. 21. While the case of using only the SEM image based on observation from the upper side has been described in the first to fourth embodiments above, a method of obtaining three-dimensional shape data by use of a tilt image will be described in the fifth embodiment.

Figure 21:
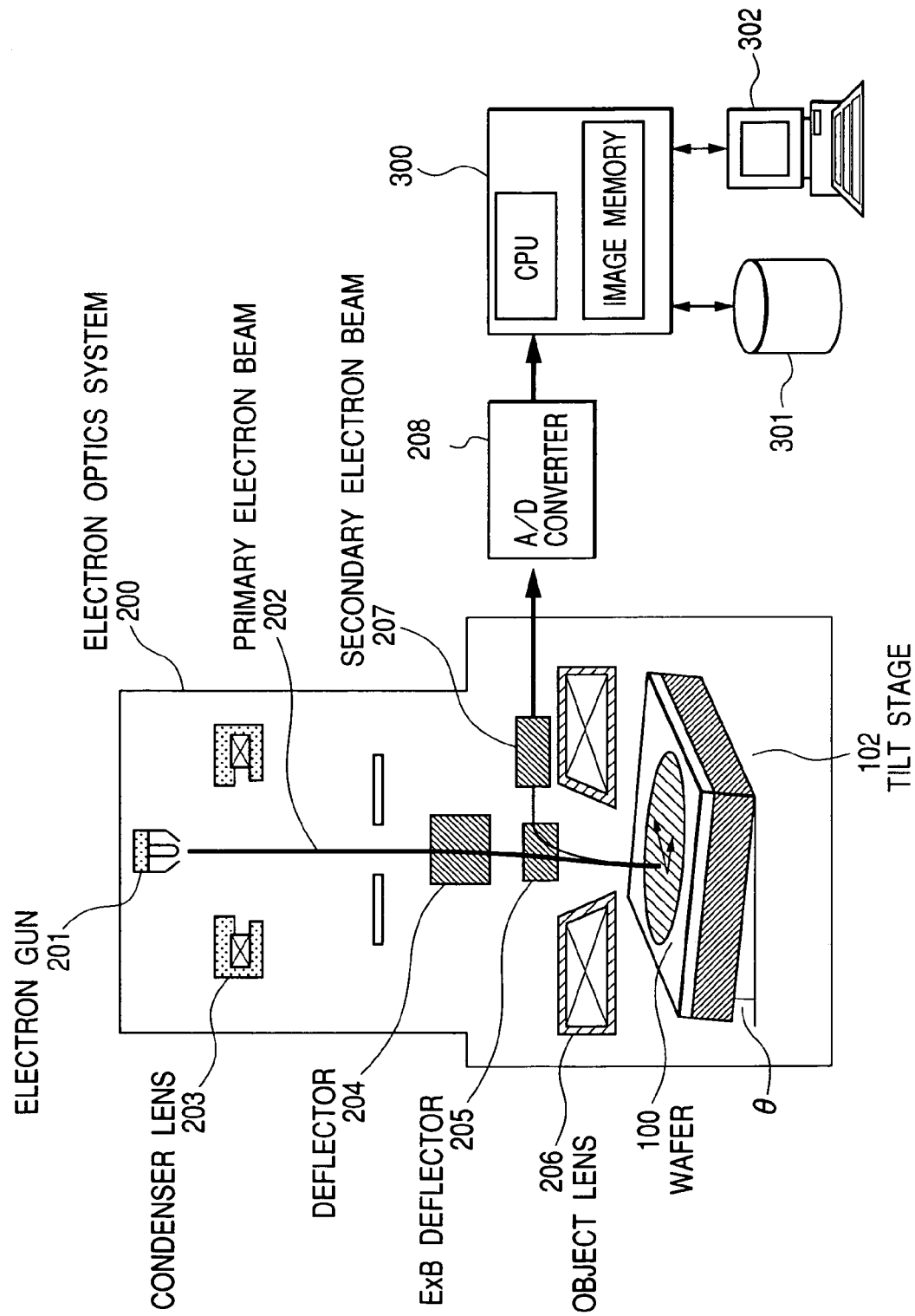
FIG. 21 illustrates an SEM having a stage tilting function in a fifth embodiment of the present invention.

As shown in FIG. 21, a CD-SEM used in this embodiment comprises a tiltable stage 102 capable of moving in an XY plane and also having a tilting function, whereby tilt images can be obtained in addition to ordinary top-down view images.

In a tilt image, the number of pixels increases in a photoresist sidewall corresponding portion on the left side and decreases in a sidewall corresponding portion on the right side (in the case where the tiltable stage is so inclined that the position of the specimen is higher on the right side). In this embodiment, attention is paid to the line profile of the photoresist sidewall corresponding portion on the side on which the number of pixels increases.

Figure 22:
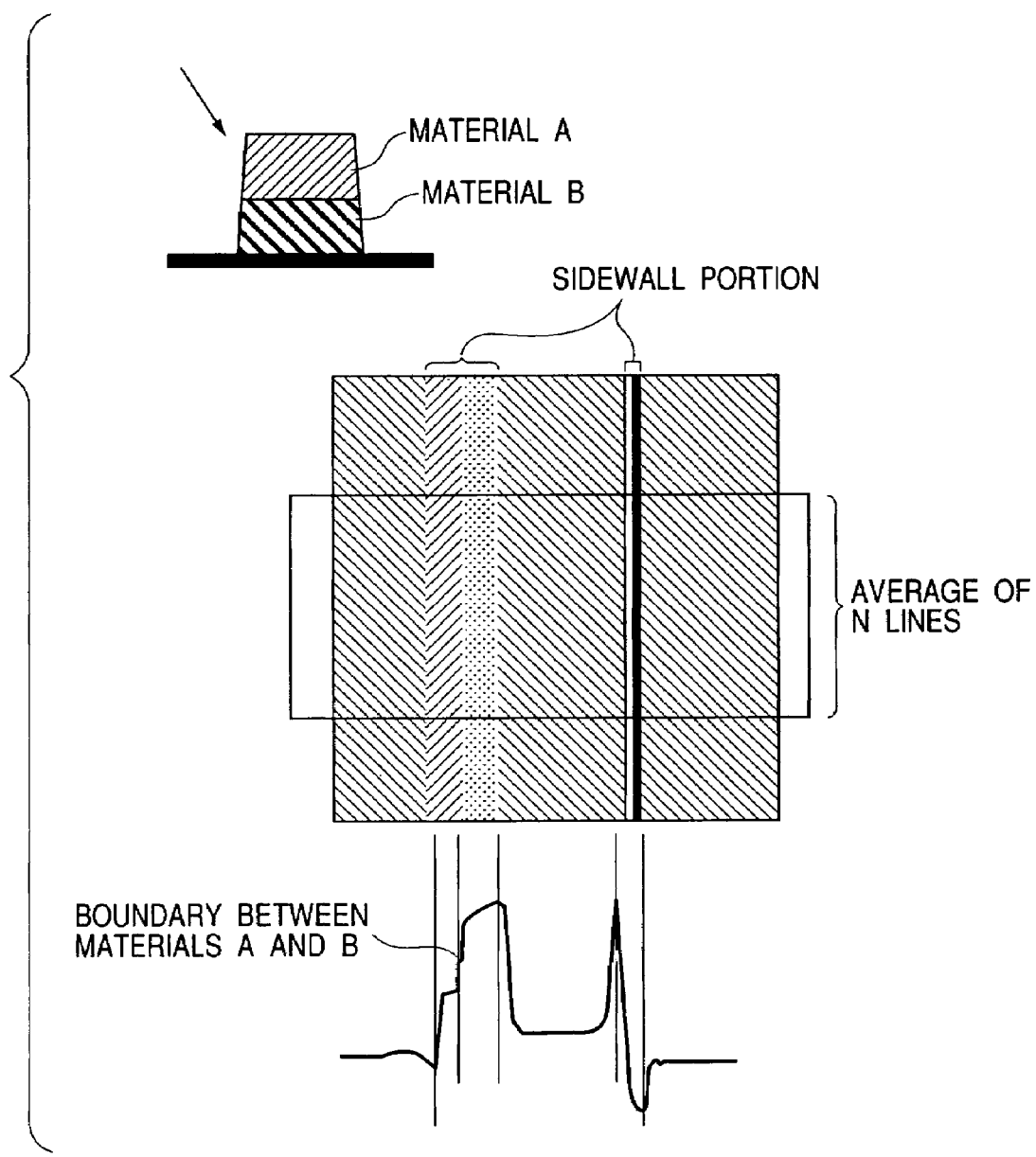
FIG. 22 illustrates a method of obtaining three-dimensional shape data by use of tilted images according to the fifth embodiment of the present invention.

When an inclined surface can be detected over a wide area, influences of the edge effect and the beam resolution can be obviated, so that shape indexes can be obtained with higher accuracy. In addition, in the case of a multi-layer film composed of a lamination of a multiplicity of different kinds of films such as poly-metal gate, a top-down view image has a small number of pixels associated with a sidewall, so that it has been difficult to detect the boundary position present in the image of the sidewall. On the other hand, when a tilt image is used as shown in FIG. 22, the boundary can be easily detected.

When the boundary position in the multi-layer film can be detected, the sectional shape of the pattern can be estimated in the same manner as in the first embodiment, based on the data on the individual film thicknesses. In the case of a multi-layer film, also, the etching conditions are changed over according to the materials of the films; therefore, determination of etching conditions and process control based on the three-dimensional shape can be performed in the same manner as in the first to fourth embodiments.

Figure 2C:
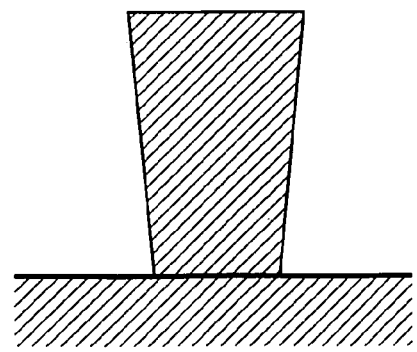
Figure 2D:
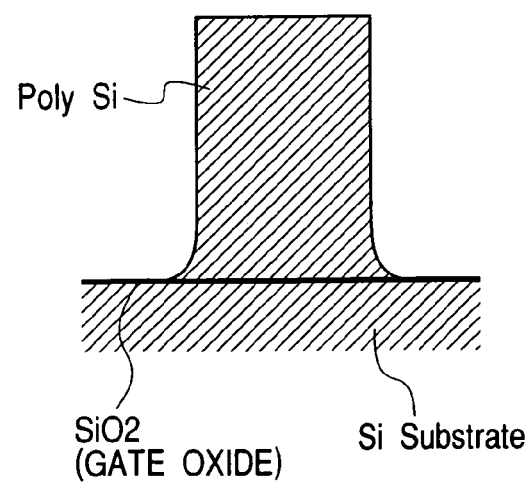
Figure 3A:
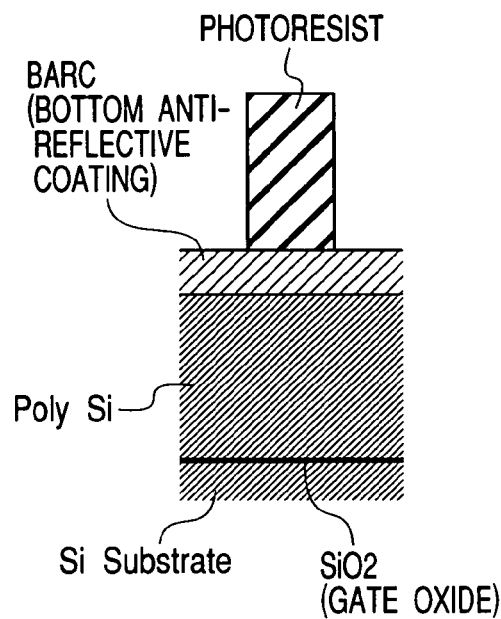
FIGS. 3A to 3E illustrate etching steps.
Figure 3B:
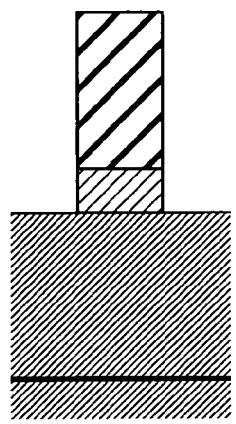
Figure 3C:
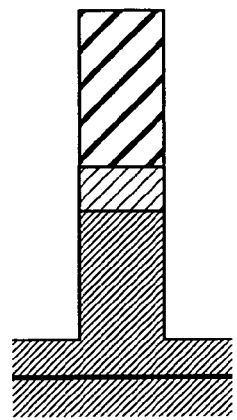
Figure 3D:
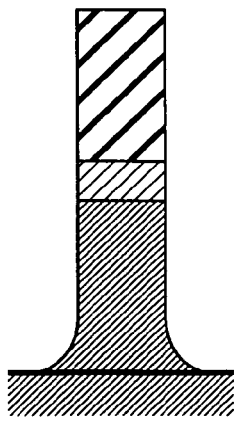
Figure 3E:
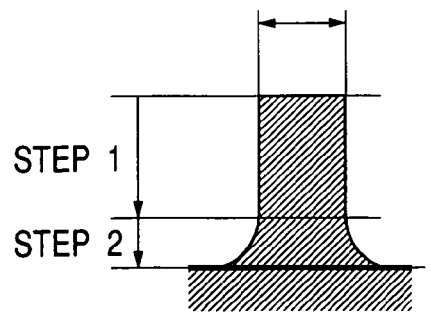

In addition, with the top-down view, it has been difficult to distinguish a retrograde shown in FIG. 2C from a normal pattern. On the other hand, tilting permits an addition of an offset to the sidewall angle index, whereby a retrograde can be detected. Further, the tilting is effective also for detection of a notch or the like generated at the bottom of the pattern.

Besides, in this embodiment, the CD-SEM makes it possible to obtain both an ordinary top-down view image and a tilt image and thereby to calculate the height of the pattern based on the principle of stereoscopy.

In the sectional shape estimating method described in the first embodiment above, the film thickness data have been utilized. However, where there is no film that functions as a stopper, such as in a device isolation step, variations in etching rate must also be detected. In this embodiment, the absolute height of the pattern can be detected directly and, therefore, it is possible to cope with such a step.

Incidentally, the tilting of the stage may be replaced by tilting of an electron optical column, or by changing the deflection angle of the electron beam so as to change the angle of incidence onto the specimen.

When the three-dimensional shape evaluation according to this embodiment is used in combination with the first to fourth embodiments, not only the same effects as in the above embodiments can be obtained, but also the use of the tilt image increases the number of pixels associated with the sidewall, whereby shape data with higher accuracy can be obtained and, accordingly, determination of etching conditions and process control can be performed more accurately. Furthermore, measurement of a retrograde, which cannot be measured using the top-down view image, can also be achieved within a certain range.

Now, a sixth embodiment will be described referring to FIG. 23. While the case of using only the SEM image based on observation from the upper side has been described in the first to fourth embodiments and the method of combining a tilt image with an ordinary top-down view image has been described in the fifth embodiment, a method of obtaining three-dimensional shape data by use of a backscattered electron image will be described in the sixth embodiment.

A CD-SEM used in the present embodiment comprises backscattered electron detectors 209 and 210 as shown in FIG. 23, and can obtain shaded images as shown in FIGS. 24A and 24B. After such shaded images are obtained, the inclination intensity of the edge of the pattern is computed from the shaded images, and this information is used in combination with the shape indexes used in the first embodiment, whereby the sidewall angle is estimated with higher accuracy.

In addition, backscattered electrons are higher in material dependency than secondary electrons, so that by utilizing this property it is possible to cope with a multi-layer film composed of lamination of different-kind films. It is generally known that a backscattered electron image shows a variation in signal amount depending on the atomic number of the object matter. Therefore, variations in signal amount appear depending on not only the difference in sidewall angle but also the difference in material. Accordingly, when a line profile is divided depending on the boundary of materials as a result of paying attention to the variation in signal amount, in the same manner as in the fifth embodiment, it is possible to estimate the sectional shape of the pattern in the same manner as in the first embodiment, based on the film thickness data. In the case of a multi-layer film, also, the etching conditions are changed over according to the material of the film, so that determination of etching conditions and process control based on the three-dimensional shape can be performed in the same manner as in the first to fourth embodiments.

Besides, as for the backscattered electrons also, a tilt image may be used to thereby detect the height of the pattern and to obtain feature indexes of the widewall, in the same manner as in the fifth embodiment.

By use of this embodiment in combination with the first to fourth embodiments, not only the same effects as above-mentioned can be obtained but also the data on the inclination intensity of the pattern edge can be additionally obtained, whereby determination of etching process conditions and process control can be performed more accurately.

According to the present invention, the three-dimensional shape of a semiconductor circuit pattern can be easily evaluated in a nondestructive manner. As a result, it is possible to greatly enhance the efficiency of determination of process conditions, which has conventionally been conducted by observation of section. In addition, the determination of process conditions, which has conventionally been conducted resorting to experience and intuition, can be easily performed based on quantitative evaluation results. Furthermore, those abnormalities in a three-dimensional shape which have been overlooked in the conventional size measurement can be detected, and production of defects in a non-reproducible etched pattern can be obviated. Moreover, a high-accuracy process control can be achieved, and a stable etching process can be provided.

The invention may be embodied in other specific forms without departing from the spirit or essential characteristics thereof. The present embodiment is therefore to be considered in all respects as illustrative and not restrictive, the scope of the invention being indicated by the appended claims rather than the foregoing description and all changes which come within the meaning and range of equivalence of the claims are therefore intended to be embraced therein.

The invention claimed is:

1. An apparatus for measuring a three-dimensional shape, comprising:
   an electron beam irradiation means for scanningly irradiating a specimen with a condensed electron beam;
   a signal detecting means comprising a secondary electron detecting unit for detecting secondary electrons generated from said specimen upon irradiation with said electron beam; and
   a signal computing means for computing a signal from said signal detecting means;
   wherein said signal computing means has the function of dividing a signal waveform obtained by said signal detecting means into a plurality of regions based on variation in the signal amount, and evaluating the three-dimensional shape of said specimen according to the sizes of said divisional regions.

2. An apparatus for measuring a three-dimensional shape as set forth in claim 1, wherein said electron beam irradiation means irradiates the surface of said specimen with said electron beam from a plurality of directions by sequentially changing the angle of incidence, and said signal computing means evaluates said three-dimensional shape by use of a plurality of electron beam signals, said plurality of electron beam signals being associated with said plurality of incidence angles which are obtained by the detection by said signal detecting means of said secondary electrons generated from said surface of said specimen irradiated with said electron beam while sequentially changing said incidence angle by said electron beam irradiation means.

3. An apparatus for measuring a three-dimensional shape as set forth in claim 1, wherein said signal detecting means further comprises a backscattered electron detecting unit for detecting backscattered electrons generated from said specimen upon irradiation with said electron beam, and said signal computing means evaluates said three-dimensional shape by use of a secondary electron signal detected by said secondary electron detecting unit and a backscattered electron signal detected by said backscattered electron detecting unit.

4. An apparatus for measuring a three-dimensional shape, comprising:
- an electron beam irradiation means for scanningly irradiating a specimen with a condensed electron beam;
- a signal detecting means comprising a secondary electron detecting means for detecting secondary electrons generated from said specimen upon irradiation with said electron beam; and
- a signal computing means for computing a signal from said signal detecting means;
- wherein said signal computing means has the function of dividing a signal waveform obtained by said signal detecting means into a plurality of regions based on variation in the signal amount, and estimating the three-dimensional shape of said specimen according to the sizes of said divisional regions.

5. An apparatus for measuring a three-dimensional shape as set forth in claim 4, wherein said electron beam irradiation means irradiates the surface of said specimen with said electron beam from a plurality of directions by sequentially changing the angle of incidence, and said signal computing means evaluates said three-dimensional shape by use of a plurality of electron beam signals, said plurality of electron beam signals being associated with said plurality of incidence angles which are obtained by the detection by said signal detecting means of said secondary electrons generated from said surface of said specimen by irradiation with said electron beam while sequentially changing said incidence angle by said electron beam irradiation means.

6. An apparatus for measuring a three-dimensional shape as set forth in claim 4, said signal detecting means further comprises a backscattered electron detecting unit for detecting backscattered electrons generated from said specimen upon irradiation with said electron beam, and said signal computing means evaluates said three-dimensional shape by use of a secondary electron signal detected by said secondary electron detecting means and a backscattered electron signal detected by said backscattered electron detecting unit.

* * * * *